United States Patent [19]

Yoa-Pu et al.

[11] Patent Number: 5,750,534
[45] Date of Patent: May 12, 1998

[54] NALBUPHINE ESTERS HAVING LONG ACTING ANALGESIC ACTION AND METHOD OF USE

[75] Inventors: Hu Oliver Yoa-Pu; Jhi-Joung Wang; Ho Shung-Tai, all of Taipei, Taiwan

[73] Assignee: National Science Council, Taipei, Taiwan

[21] Appl. No.: 690,361

[22] Filed: Jul. 26, 1996

Related U.S. Application Data

[63] Continuation-in-part of Ser. No. 161,257, Mar. 16, 1994, abandoned.
[51] Int. Cl.$^6$ .................... A61K 31/44; A61K 31/485
[52] U.S. Cl. .................................................. 514/282
[58] Field of Search ................................. 514/282

[56] References Cited

U.S. PATENT DOCUMENTS 4,673,679  6/1987  Aungst et al. ................ 514/282

*Primary Examiner*—William R. A. Jarvis
*Attorney, Agent, or Firm*—Bucknam and Archer

[57] ABSTRACT

Long acting analgesic nalbuphine prodrugs, and pharmaceutical composition comprising the nalbuphine prodrugs are described. These prodrugs are long-acting injectable analgesics when administered intramuscularly, subcutaneously, orally, or transdermally.

15 Claims, 35 Drawing Sheets

BUPRENORPHINE

MORPHINE

FIG. 4 B

PPM

| | | | | |
|---|---|---|---|---|
| 7.24108 | 6.75476 | 6.72715 | 6.61307 | 6.58613 |
| 4.61158 | 4.59427 | 4.13531 | 3.15375 | 3.14173 |
| 3.09533 | 3.03374 | 2.79660 | 2.77691 | 2.66471 |
| 2.64456 | 2.60624 | 2.58206 | 2.55663 | 2.53162 |
| 2.46520 | 2.43946 | 2.41552 | 2.35097 | 2.24833 |
| 2.20764 | 2.19700 | 2.18639 | 2.17166 | 2.14084 |
| 2.05874 | 2.04676 | 2.03466 | 1.90583 | 1.87862 |
| 1.85362 | 1.84149 | 1.82530 | 1.77690 | 1.64328 |
| 1.62039 | 1.59217 | 1.56831 | 1.54946 | 1.51157 |
| 1.49395 | 1.47112 | 1.44459 | 1.42389 | 1.40539 |
| 1.25462 | 1.22988 | 1.20465 | | |

FIG. 5C

MASS SPECTRUM 03/12/91 14:58:00+ 0:55
SAMPLE:NAL-C3
CONDS.:+/EI/Q1
MASS SPECTRUM/DIRECT PROBE(70EV)
54 TO #57 SUMMED

DATA:91031218   #55
BASE M/Z: 358
CALI:910312CAQ1   #1
RIC:530432.

FIG. 6 B

| λ | ABS | λ | ABS |
|---|---|---|---|
| 400.0 | -0.004 | 395.0 | -0.002 |
| 390.0 | -0.003 | 385.0 | -0.003 |
| 380.0 | -0.004 | 375.0 | -0.003 |
| 370.0 | -0.003 | 365.0 | -0.003 |
| 360.0 | -0.004 | 355.0 | -0.003 |
| 350.0 | -0.004 | 345.0 | -0.004 |
| 340.0 | -0.002 | 335.0 | -0.000 |
| 330.0 | 0.006 | 325.0 | -0.008 |
| 320.0 | -0.073 | 315.0 | -0.077 |
| 310.0 | -0.069 | 305.0 | -0.053 |
| 300.0 | 0.003 | 295.0 | 0.065 |
| 290.0 | 0.094 | 285.0 | 0.099 |
| 280.0 | 0.096 | 275.0 | 0.094 |
| 270.0 | 0.088 | 265.0 | 0.089 |
| 260.0 | 0.089 | 255.0 | 0.094 |
| 250.0 | 0.095 | 245.0 | 0.097 |
| 240.0 | 0.103 | 235.0 | 0.107 |
| 230.0 | 0.114 | 225.0 | 0.123 |
| 220.0 | 0.130 | 215.0 | 0.225 |
| 210.0 | 1.046 | 205.0 | 0.761 |
| 200.0 | 0.351 | | |

FIG. 7 B

PPM

| | | | | |
|---|---|---|---|---|
| 7.24067 | 6.73684 | 6.70964 | 6.61034 | 6.58302 |
| 4.60722 | 4.58993 | 4.12457 | 3.21412 | 3.20088 |
| 3.09327 | 3.03164 | 2.79347 | 2.77361 | 2.66229 |
| 2.64223 | 2.60072 | 2.58060 | 2.46364 | 2.43817 |
| 2.41624 | 2.37897 | 2.34884 | 2.24450 | 2.20356 |
| 2.18455 | 2.16787 | 2.13861 | 2.06931 | 2.05717 |
| 2.04461 | 2.03285 | 2.01303 | 1.96663 | 1.93954 |
| 1.90382 | 1.87650 | 1.86665 | 1.85082 | 1.83959 |
| 1.82384 | 1.81176 | 1.77510 | 1.64021 | 1.61651 |
| 1.58809 | 1.56436 | 1.54611 | 1.53237 | 1.50376 |
| 1.48580 | 1.44990 | 1.44033 | 1.41944 | 1.39970 |
| 1.38272 | 1.34670 | 1.32152 | | |

FIG. 8B

PERKIN-ELMER 983
DATE 80,4,3
SAMPLE NaI-Pival
OPERATOR REPLOTTED SPECTRUM
SCAN MODE 4
NOISE FILTER 1
RESOLUTION 3.0
ORDINATE MODE %T
ORD HIGH 75.00
ORD LOW 20.00
RANGE 4000.0-400.0
ABSC SCALE 0.50

PEAK THRESHOLD 2

| CM -1 | %T | CM -1 | %T | CM -1 | %T |
|---|---|---|---|---|---|
| 3528 0 | 52.79 | 3477 0 | 40.65 | 3345 0 | 48.80 |
| 3010 0 | 58.43 | 2934 0 | 32.81 | 2909 0 | 33.27 |
| 2836 0 | 43.78 | 1722 0 | 26.96 | 1597 0 | 53.98 |
| 1463 0 | 41.81 | 1436 0 | 33.76 | 1384 0 | 39.76 |
| 1356 0 | 44.64 | 1338 0 | 46.20 | 1308 0 | 49.16 |
| 1272 0 | 41.84 | 1256 0 | 45.49 | 1225 0 | 37.75 |
| 1199 0 | 48.33 | 1148 0 | 36.37 | 1135 0 | 37.09 |
| 1108 0 | 22.46 | 1045 0 | 33.54 | 991 0 | 41.89 |
| 970 0 | 41.28 | 933 0 | 46.04 | 906 0 | 50.02 |
| 884 0 | 52.90 | 856 0 | 46.81 | 834 0 | 60.13 |
| 823 0 | 58.60 | 808 0 | 52.99 | 777 0 | 48.51 |
| 759 0 | 56.99 | 747 0 | 55.40 | 730 0 | 61.12 |
| 705 0 | 55.60 | 626 0 | 52.76 | | |

FIG. 9 B

PPM
7.24111  6.75672  6.72890  6.61910  6.59213
4.61597  4.59865  4.13502  3.16159  3.10107
3.03955  2.80247  2.78269  2.66946  2.64920
2.60783  2.56194  2.53683  2.51219  2.47106
2.19368  2.17679  2.05232  1.91339  1.88529
1.85969  1.74680  1.72283  1.69778  1.59827
1.45174  1.41364  1.31914  1.29724  0.90011
0.87792

FIG. 10 B

MASS SPECTRUM
01/22/91  11:24:00+ 1:08
SAMPLE: NAL-C7
CONDS.: +/EI/Q1
MASS SPECTRUM/DIRECT PROBE(70EV)
68 TO #69 SUMMED

DATA: 91012211  #68
BASE M/Z: 414
CALI:91012CQ1  #1
RIC:287232.

FIG. 11 B

PPM

| | | | | |
|---|---|---|---|---|
| 171.771 | 148.502 | 132.997 | 131.435 | 130.663 |
| 121.585 | 118.773 | 91.573 | 77.640 | 77.003 |
| 76.369 | 70.093 | 66.583 | 62.906 | 60.542 |
| 46.056 | 43.771 | 33.985 | 33.563 | 31.924 |
| 29.896 | 29.591 | 29.443 | 29.352 | 29.257 |
| 29.080 | 28.996 | 26.982 | 26.775 | 26.243 |
| 24.883 | 24.761 | 23.927 | 23.396 | 22.681 |
| 18.710 | 14.120 | -.015 | | |

NC.003
DATE   3-0-0

| | | | |
|---|---|---|---|
| SF | 50.323 | FW | 19000 |
| SY | 50.0 | O2 | 3200.000 |
| O1 | -12.462 | DP | 16L CPD |
| S1 | 32768 | | |
| TD | 32768 | LB | 0.0 |
| SW | 15151.515 | GB | 0.0 |
| HZ/PT | .925 | CX | 30.00 |
| | | CY | 0.0 |
| PW | 2.0 | F1 | 189.998P |
| RD | 3.000 | F2 | -2.994P |
| AQ | 1.081 | HZ/CM | 323.733 |
| RG | 400 | PPM/CM | 6.433 |
| NS | 15244 | SR | -6682.03 |
| TE | 297 | | |

FIG. 12B

PPM

| | | | | |
|---|---|---|---|---|
| 171.728 | 148.499 | 132.976 | 131.436 | 130.641 |
| 129.866 | 121.591 | 118.758 | 91.546 | 77.645 |
| 77.010 | 76.375 | 70.115 | 68.581 | 62.933 |
| 60.548 | 46.051 | 43.763 | 36.608 | 33.978 |
| 33.575 | 31.890 | 29.751 | 29.551 | 29.297 |
| 28.992 | 27.186 | 26.963 | 26.768 | 26.233 |
| 24.873 | 24.661 | 23.991 | 23.391 | 22.663 |
| 18.697 | 14.101 | -.031 | | |

YSL.000
DATE 12-0-0

| | | | |
|---|---|---|---|
| SF | 50.323 | LB | 3.000 |
| SY | 50.0 | GB | 0.0 |
| O1 | -12.462 | CX | 30.00 |
| S1 | 32768 | CY | 0.0 |
| TD | 32768 | F1 | 230.004P |
| SW | 15151.515 | F2 | -4.997P |
| HZ/PT | .925 | HZ/CM | 394.201 |
| | | PPM/CM | 7.833 |
| | | SR | -6682.03 |

PW 2.0
RD 3.000
AQ 1.081
RG 400
NS 2624
TE 297

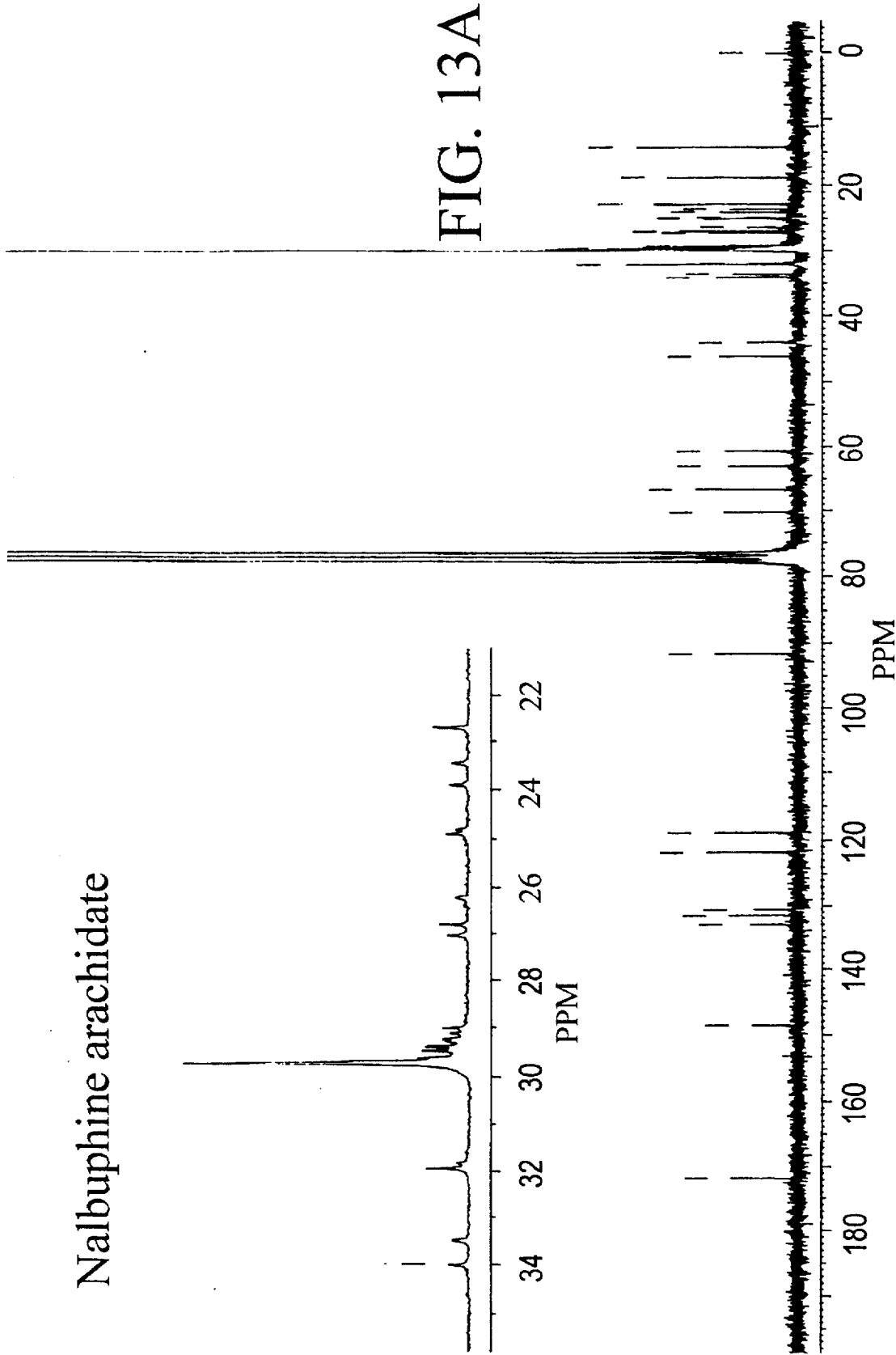

FIG. 13 B

PPM

| | | | | |
|---|---|---|---|---|
| 171.770 | 148.524 | 132.946 | 131.487 | 130.484 |
| 121.657 | 118.786 | 91.535 | 148.525 | 77.644 |
| 77.203 | 77.008 | 76.374 | 66.563 | 62.911 |
| 60.502 | 45.968 | 43.898 | 33.986 | 33.487 |
| 31.798 | 29.894 | 29.590 | 29.444 | 29.361 |
| 29.260 | 29.215 | 29.098 | 28.998 | 27.018 |
| 26.796 | 26.205 | 24.882 | 24.802 | 23.895 |
| 23.449 | 22.685 | 18.710 | 14.132 | -.016 |

NC.001
DATE    29-19-0

| | | | |
|---|---|---|---|
| SF | 50.323 | FW | 19000 |
| SY | 50.0 | O2 | 3200.000 |
| O1 | -12.462 | DP | 16L CPD |
| S1 | 32768 SR | | |
| TD | 32768 | LB | 0.0 |
| SW | 15151.515 | GB | 0.0 |
| HZ/PT | .925 | CX | 30.00 |
| | | CY | 0.0 |
| PW | 2.0 | F1 | 200.013P |
| RD | 3.000 | F2 | -4.978P |
| AQ | 1.081 | HZ/CM | 343.862 |
| RG | 400 | PPM/CM | 6.833 |
| NS | 21752 | SR | -6682.03 |
| TE | 297 | | |

NALBUPHINE ESTERS HAVING LONG ACTING ANALGESIC ACTION AND METHOD OF USE

This application is a Continuation-in-Part of U.S. Ser. No. 08/161,257 filed Mar. 16, 1994, now abandoned.

FIELD OF THE INVENTION

This invention relates to long acting analgesic nalbuphine prodrugs and to pharmaceutical compositions containing these compounds.

BACKGROUND OF THE INVENTION

An ideal analgesic should exhibit short onset time, should be long acting, potent, should cause no addiction, no inhibition of the cardiac or cardiovascular system, no respiratory inhibition, and should have few other adverse effects. For the relief of pain, local anesthetics like xylocaine or bupivacaine can only be applied to restricted areas. In addition, local anesthetics are short acting and even when they are given intracerebroventricularly, the duration of action hardly exceeds 6 hours. Therefore, for the severe and acute pain caused by cardiac, pulmonary, abdominal, osteopathia, and obstetrical surgery, severe burn injury and-terminal stage of cancer, local anesthetics are not satisfactory.

Non-narcotic analgesics, such as aspirin and acetaminophen, relieve pain of only low intensity, such as pain due to headache or toothache but they do not help in the case of severe pain. For the pain of high intensity and widespread in origin, narcotic analgesics are certainly indicated. Morphine, meperidine, fentanyl interacting with specific receptors (i.e. mu receptor) in the CNS are narcotic analgesics and exhibit potent analgesic activity. Hayes, A. G. et al. (Br. J. Pharmacol. Vol 79, 731, 1983) have reported that all the narcotic analgesics exhibit the same disadvantages with respect to addiction, and respiratory inhibition. For the long term use, addiction is the most unwanted problem and severe respiratory depression and death often occur in patients with poor respiratory function or post cardiac and chest surgery. In addition, the duration of action of the narcotic analgesics is somewhat short. In order to maintain the analgesic effect, the dosing interval needs to be set at 3–5 hours. Even when the agent is administered to the spinal marrow, the duration of action could not be longer than 48 hours. With larger amounts of the narcotic analgesic, e.g. morphine, 0.5–1.0 mg/dose to prolong the effect, as described in the literature published by Baxter, A. D. et al (Can. J. Anesth. Vol 36, 503, 1989), fatal respiratory depression is likely to occur.

Recently a new type of opiods, so-called narcotic agonist-antagonist analgesics have been developed. The typical ones such as nalbuphine, buprenorphine are shown in FIGS. 2(A) and 2(B). They exhibit a dual action of agonism and antagonism on opiods-receptors as reported by Schmidt, W. K. et al (Drug Alcohol Depend. Vol 14, 339, 1985). For instance, nalbuphine is the antagonist of the mu receptor and is the agonist of the kappa receptor as well. After a six-month treatment, nalbuphine showed no significant addiction with only slight respiratory inhibition. Due to these pharmacological properties, the adverse effects associated with the narcotic analgesics have greatly improved. They decrease the incidence of addiction and diminish the inhibitory effect on the respiratory system. Shafer, S. L. et al. have investigated the analgesic potency of this new type of narcotic analgesics. They have found that when compared with the more traditional types to elicit the same analgesic effect, the dose needed for morphine is 10 mg; for buprenorphine is 0.3 mg; for nalbuphine is 10 mg; for butorphanol is 2 mg (Anesthesiology, Vol. 74, 53, 1991). According to the publication by Schmidt, W. K. et al, supra (1985), nalbuphine is the most widely used one and has excellent therapeutic efficacy. After continuous use of nalbuphine for 6 months, no significant addiction was found. This new type of analgesics exhibits only slight respiratory inhibition. In clinical use, nalbuphine is safer than the traditional narcotic analgesics.

Nalbuphine has been found to be effective in control of severe and deep pain caused by cardiac, pulmonary, abdominal, osteopathia, and obstetrical surgery, severe burn injury and the terminal stages of cancer via various administration routes, such as intramuscular, intravenous, intrathecal (Schmidt, W. K. et al., 1985). The only drawback in the case of nalbuphine is the short duration of action. Wang, J. J. et al. (Ma. Tsui. Hsueh. Tsa. Chi., Vol 23, 3, 1985) have reported that the effect of nalbuphine can only be sustained for 3–5 hours after intravenous administration and 6–8 hours by intrathecal injection. However, severe pain usually cannot be relieved in such short periods of time.

Therefore, any improvement in extending the duration of action of nalbuphine would be a great breakthrough in medicine and at the same time would provide a more economical therapeutic system. The prodrug approach is widely used to increase the duration of drugs that are rapidly eliminated. The antipsychosis agent, haloperidol, is one example. Hemstrom, C. A. et al. (Drug Intell. Clin. Pharm., Vol. 22, 290, 1988) have found that the dosing interval of haloperidol decanoate can be prolonged from 2–4 times a day to 1–2 times a month. Joshi, J. V. et al. (Steroids, Vol. 53, 571, 1989) also reported that the prodrug of northisterone enanthate can be given once every 2 months.

Broekkamp, C. L. et al. (J. Pharm. Pharmacol., Vol. 40, 434, 1988) have proposed the long-acting mechanism of action of ester-type prodrugs. They are esterified with fatty acids of different carbon numbers resulting in an increase in lipophilicity of the prodrugs. Therefore, when prodrugs are given intramuscularly, the release rates are decreased and the duration of action is prolonged. Ester-type prodrugs are hydrolyzed by esterases in the body resulting in the increase of the mother compounds. Esterase exists in many tissues and organs, such as blood, brain, liver, heart, lungs, kidneys, and muscles. The pharmacological effect and safety of the ester-type prodrug and the mother compound are reported to be the same (Gelders, Y. G. et al., Int. Clin. Psychopharmacol., Vol. 1, 1, 1986).

SUMMARY OF THE INVENTION

The object of this invention is to provide nalbuphine esters which have longer duration of action and same activity as nalbuphine so that they may be used in the treatment of living subjects including humans affected by serious pain.

Morphine is a narcotic analgesic with addiction effect. Its structure is shown in FIG. (3). Broekkamp, C. L. et al (1988) have stated that esterification of the phenol group on carbon atom 3 of the morphinan ring makes the esterified derivatives which have the following characteristics. (1) increased lipophilicity, (2) low affinity to morphine receptors, (3) the side effects are decreased, but released parent drugs have the same pharmacological activity, (4) the effect and safety of esterified compounds and mother compounds are the same.

It is also possible to decrease the release rate and the side effects of a narcotic analgesic using subcutaneous administration. The subcutaneous area has less blood flow and more fatty tissue than other portions of the body so that the ester-type prodrugs are slowly hydrolyzed by esterases in subcutaneous areas. When using the intracerebroventricular or spinal cord administration, Rutter, D. V. et al. (Br. J. Anesth., Vol. 53, 915, 1981) also studied the increase of the duration of action and the increase of side effects of narcotic analgesics such as Morphine, Fentanyl, Burprenorphine, Nalbuphine. Other than those administration methods described above, the percutaneous method is also favorable. Hill, H. F. et al. (Eur. J. Pharmacol., Vol. 119, 23, 1985) have proposed the percutaneous administration of Fentanyl, but the Fentanyl percutaneous dosage form safety range is 0.6–3 µg/ml the same as the narcotic analgesics of Mu receptor. Bruce et al. in U.S. Pat. No. 4,673,679 issued Jun. 16, 1987 state that Morphine, Fentanyl, Burprenorphine, Nalbuphine derivatives exhibit enhanced bioavailability from sublingual, buccal, nasal dosage form but they did not investigate the analgesic action and the long acting effect of Nalbuphine prodrugs and specific dosage forms as have not been described.

Nalbuphine prodrugs are relatively new analgesics as shown in FIG. (1) in which R group is R'CO, R' denotes $C_nH_{2n-1}$ $C_nH_{2n+1}$ and the carbon number is 20 to 40. They not only possess the potent analgesic activity of the commonly used analgesics but also minimize the side effects, such as addiction and respiratory depression associated with the traditional narcotics. The present invention also covers various formulations capable of prolonging the release of nalbuphine and the design of nalbuphine prodrugs by modifying the chemical structure of nalbuphine. The nalbuphine prodrugs are characterized by (1) long-acting, i.e. when given parenterally, (for example, intramuscularly) the dosing interval can be altered from every four hours to several days, even longer, (2) low first-pass effect and high bioavailability when given orally.

BRIEF DESCRIPTION OF THE DRAWINGS

The present invention is illustrated by reference to the accompanying drawings of which:

FIGS. 4A–B shows $^1$H-NMR chart of nalbuphine propionate

FIGS. 5A–C shows the mass spectroscopy MS chart and UV chart of nalbuphine propionate FIGS. 7A–B is $^1$H-NMR chart of nalbuphine pivalate FIGS. 8A–B is IR chart of nalbuphine pivalate FIGS. 9A–B is the $^1$H-NMR chart of nalbuphine enanthate FIGS. 10A–B is the MS chart of nalbuphine decanoate FIGS. 11A–B is $^{13}$C-NMR chart of nalbuphine behenate FIGS. 12A–B is $^{13}$C-NMR chart of nalbuphine erucicate FIGS. 13A–B is $^{13}$C-NMR chart of nalbuphine arachidate

The preferred nalbuphine prodrugs are prepared from propionic acid, benzoic acid, enanthic acid, n-valeric acid, pivalic acid, decanoic acid and saturated fatty acids, such as lauric acid, stearic acid, arachidic acid, cerotic acid, etc. and unsaturated fatty acid, such as oleic acid, linolenic acid, undecylenic acid, cinnamic acid, etc. In FIG. 1 (1), R is the residue of the fatty acid denoted by R'CO, in which R' represents a saturated or unsaturated alkyl group $C_nH_{2n-1}$, $C_nH_{2n+1}$, n is an integer from 1 to 40 and is selected from the groups consisting of (a) straight chain alkyl groups, (b) branched-chain alkyl groups, (c) straight chain alkyl groups attached to the benzene ring (d) branched chain alkyl groups attached to the benzene ring.

The nalbuphine prodrugs synthesized by the above mentioned methods have been identified by nuclear magnetic resonance (NMR), infrared (IR) and ultraviolet (UV) spectroscopy, gas chromatography/mass spectrometry (GC/MS), elementary analysis and then formulated into different dosage forms as desired. The suitable dosage forms of nalbuphine prodrugs can be oral preparations, injectable oily formulations with sesame oil, soybean oil, or peanut oil as the vehicle of injection. The injectable oily preparations can be given by the intracerebroventricular, intramuscular, subcutaneous, spinal marrow routes. The nalbuphine prodrugs may also be formulated and administered by percutaneous, buccal, sublingular, topical route as pastes, ointments, suppositories.

In this invention, a novel animal model for testing the antinociceptive actions of analgesics has also been established. Traditionally, analgesics are evaluated by infrared tail-flick, hot water tail-flick, hot plate tests or writhing tests. However, those animal models have proved to be inapplicable for narcotic agonist-antagonists such as buprenorphine, nalbuphine and butorphanol (Shaw, J. S., Br. J. Pharmacol. Vol. 195, 578, 1988). Besides, the animals usually died after performing the writhing test. Therefore, the writhing test is not suitable for testing long-acting analgesics. In the present animal model, nociceptive thresholds were measured before and after the drug dosing as the latency for the Sprague-Dawley rat to flick or remove its tail from the cold ethanol (−20° C.) bath after immersion. This latency was used as an indicator for the duration of action of the tested analgesic. This animal model is the so-called rat cold ethanol tail-flick test.

Figure 1:
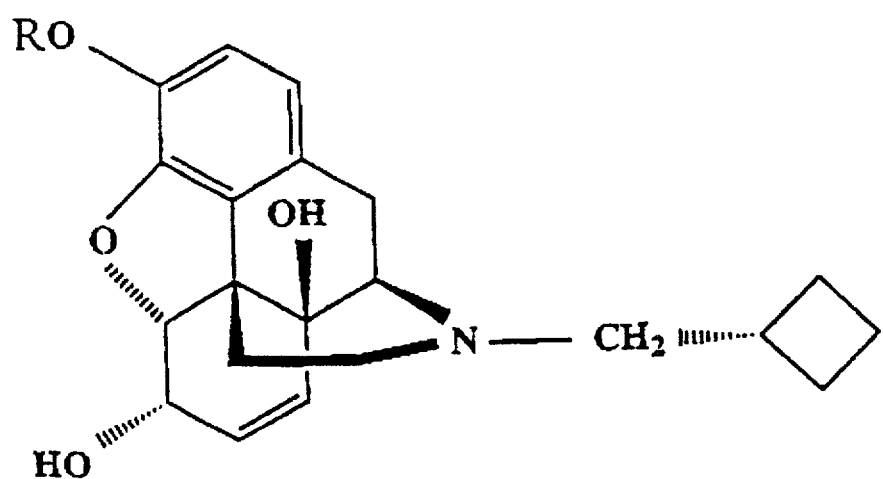
FIG. 1 shows the structure of Nalbuphine prodrugs
Figure 2A:
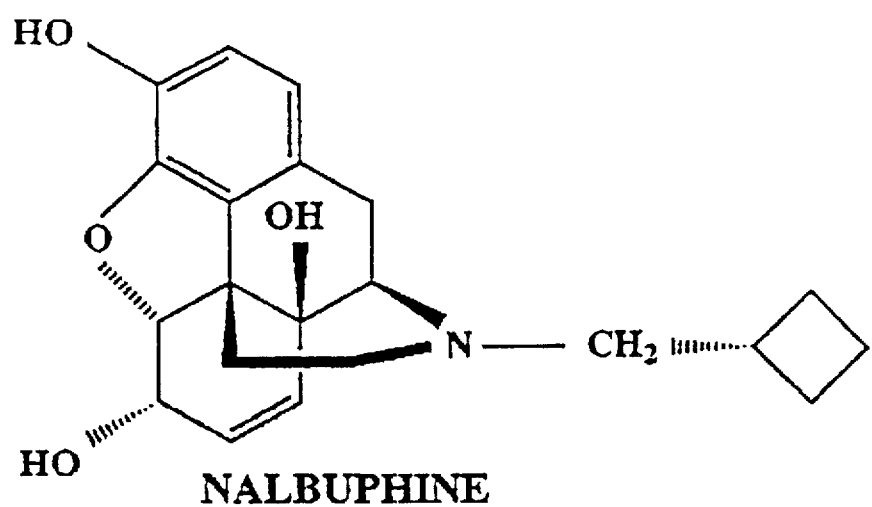
FIG. 2(A) shows the structure of Nalbuphine
Figure 2B:
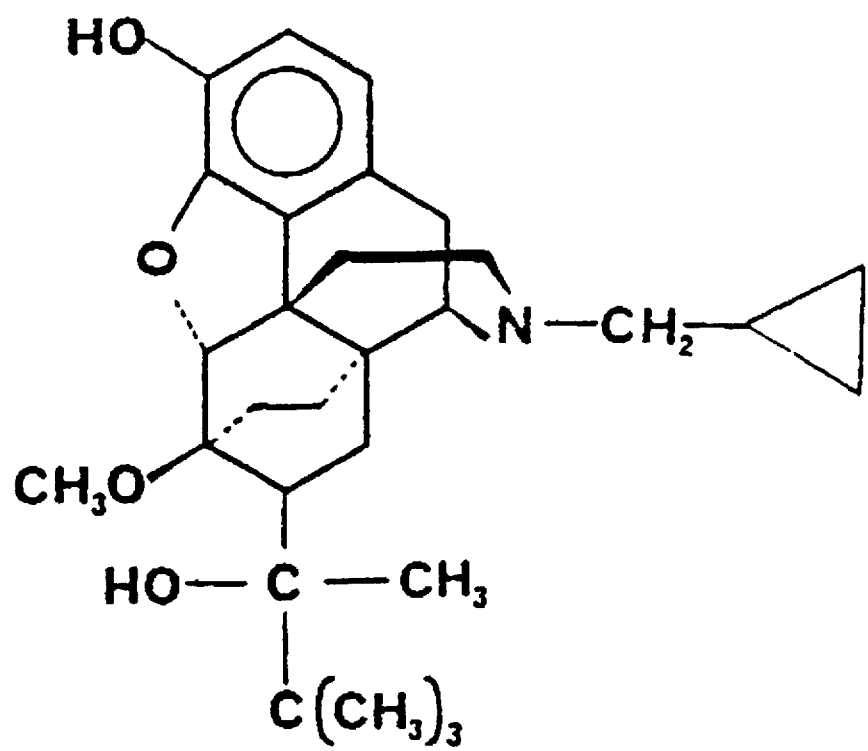
FIG. 2(B) shows the structure of Buprenorphine
Figure 3:
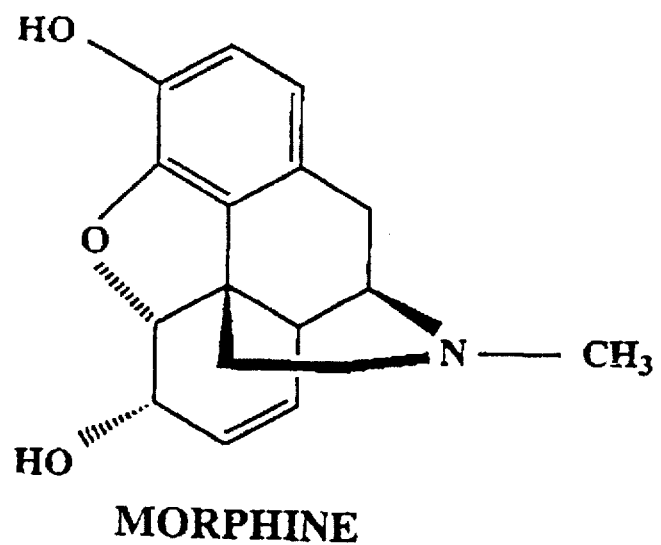
FIG. 3 shows the structure of Morphine
Figure 4A:
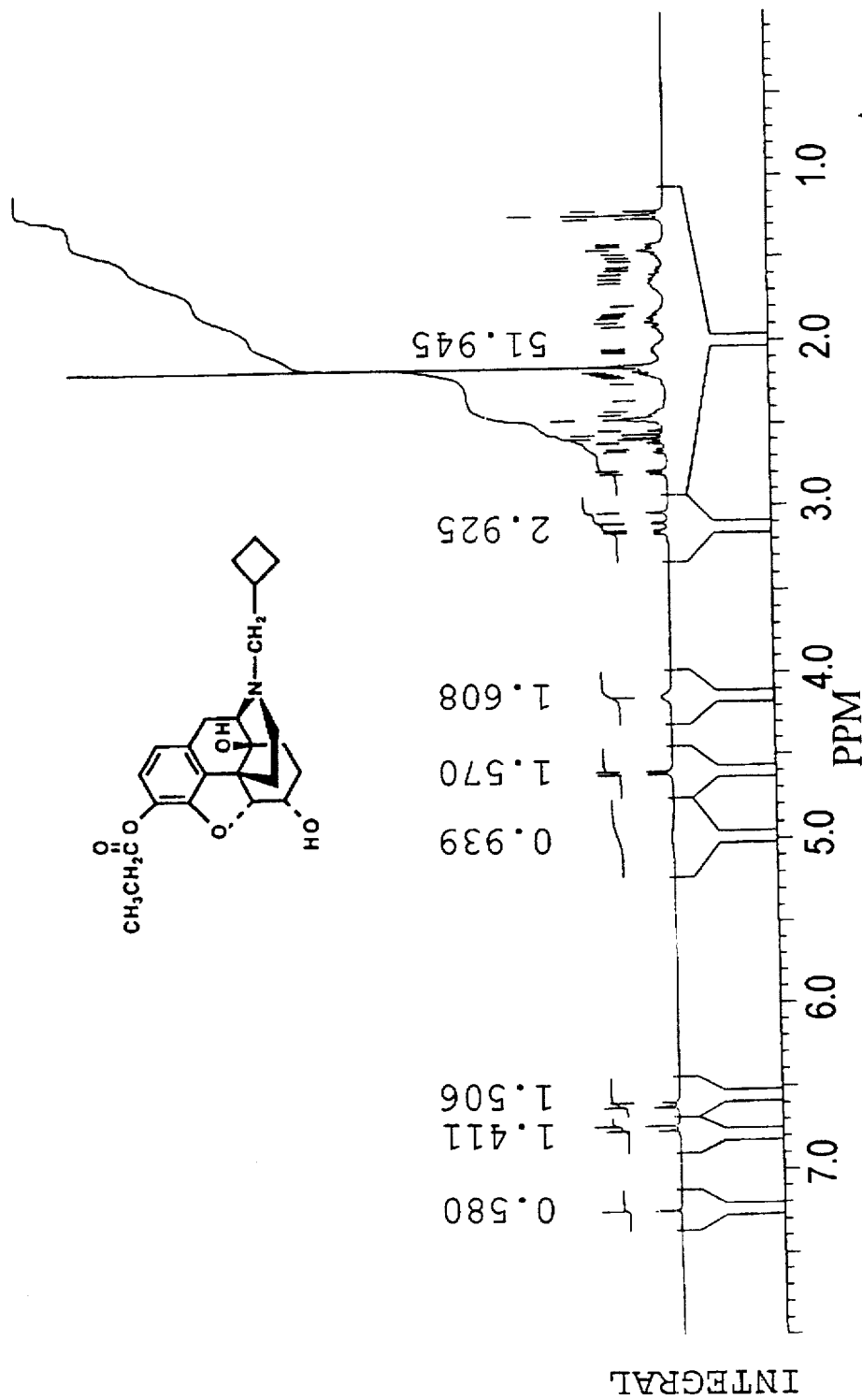
Figure 5A:
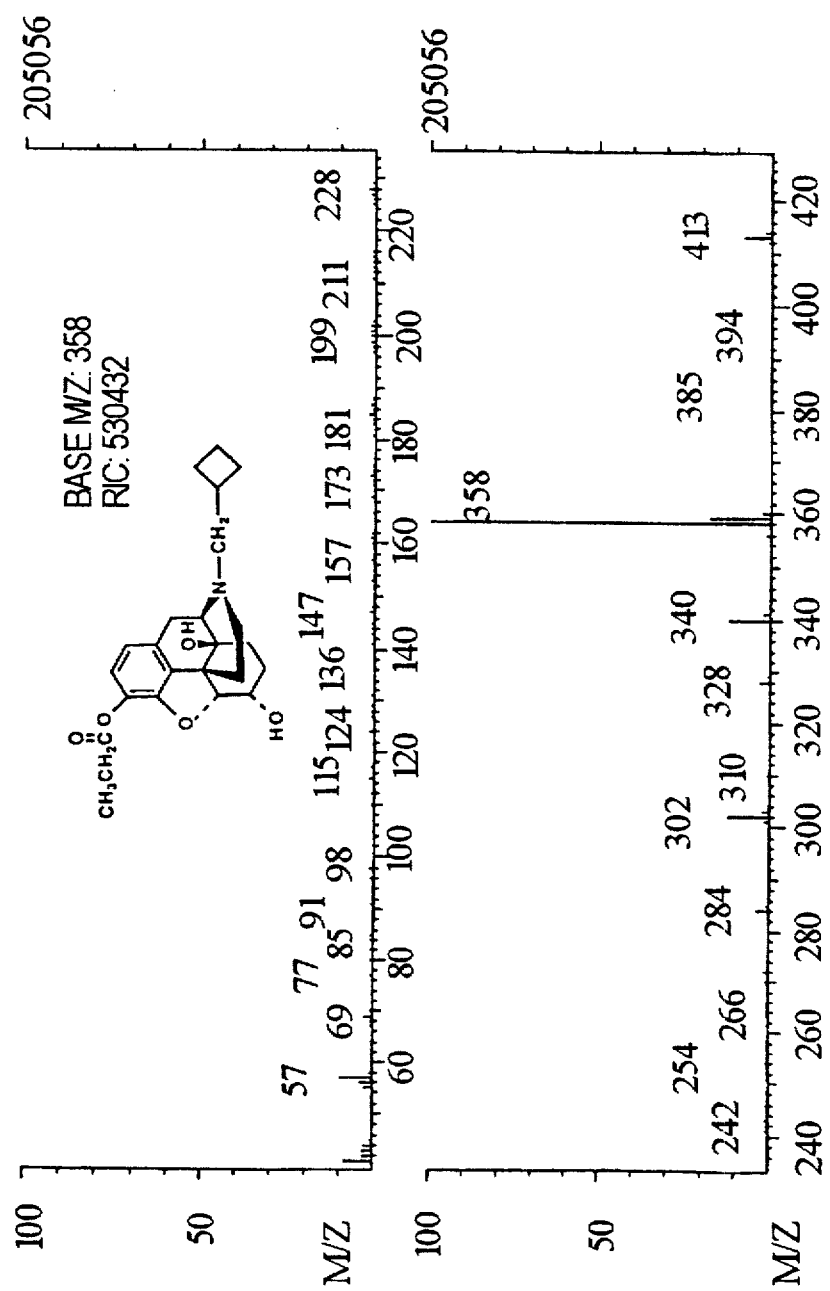
Figure 5B:
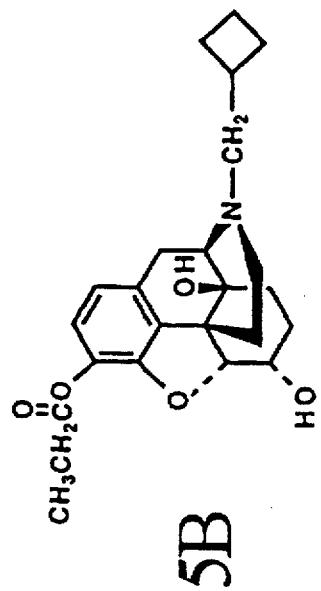
Figure 5B:
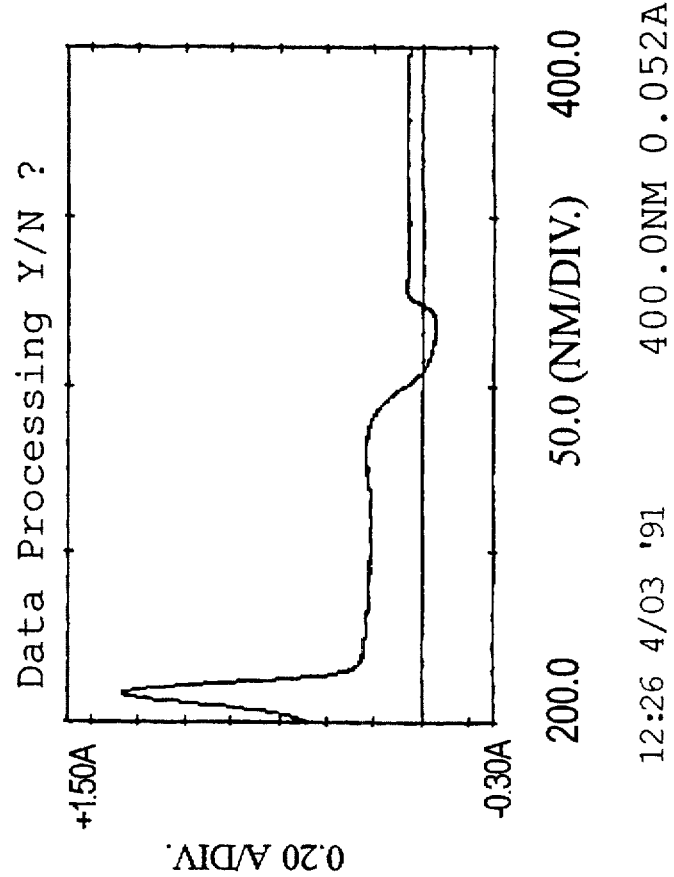

EXAMPLE 1
Preparation of Nalbuphine Propionate 75 mL of methylene chloride and 3.75 g (0.01 mole) of nalbuphine were added to a 250-mL round-bottomed flask. The flask was placed in an ice bath to keep it cool. The content was then stirred and then gradually a 20 mL of methylene chloride solution containing 0.16 mole of triethylamine was added. With rapid stirring, another 20 mL of methylene chloride solution containing 0.011 mole of dry propionic anhydride was added drop by drop. Afterward, the mixture was stirred at room temperature for 1 hour. 20 mL of 10% sodium carbonate solution was added to neutralize the residual acid and remove the water soluble impurities. Sodium sulfate was used to dehydrate the solution. After drying under vacuum, a nalbuphine propionate solid was obtained. The product was purified by column chromatography. The physical data are shown in Table 1 and FIGS. 4 and 5.

Figure 6:
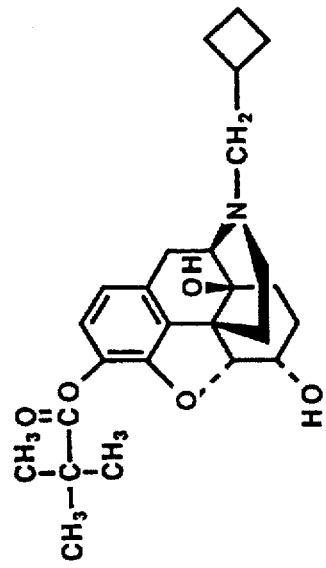
FIGS. 6A–B shows the chart and UV chart of nalbuphine pivalate
Figure 6:
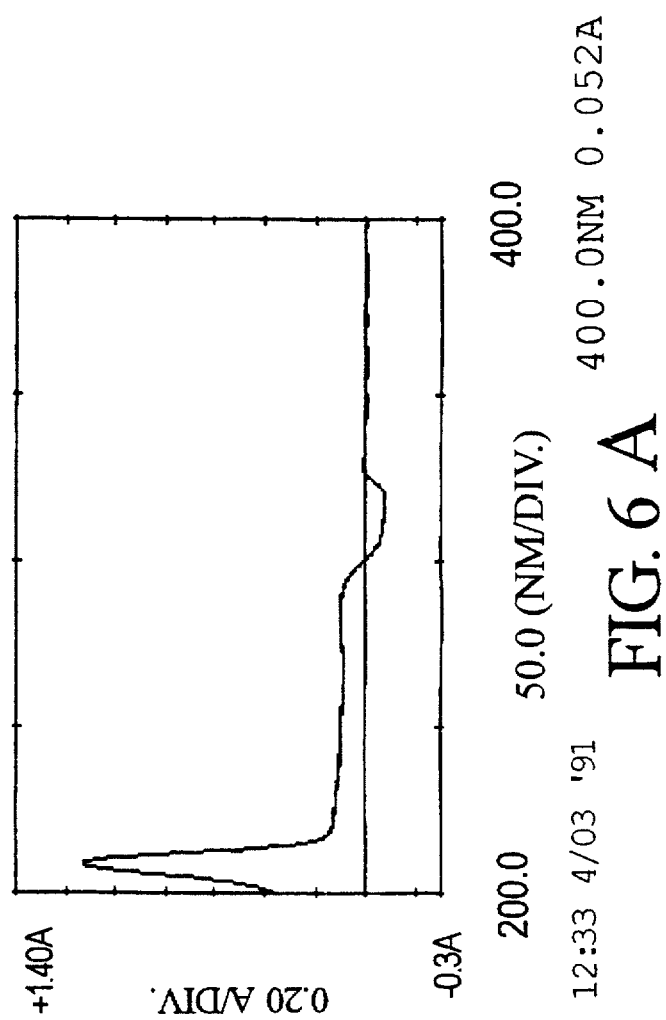
Figure 7A:
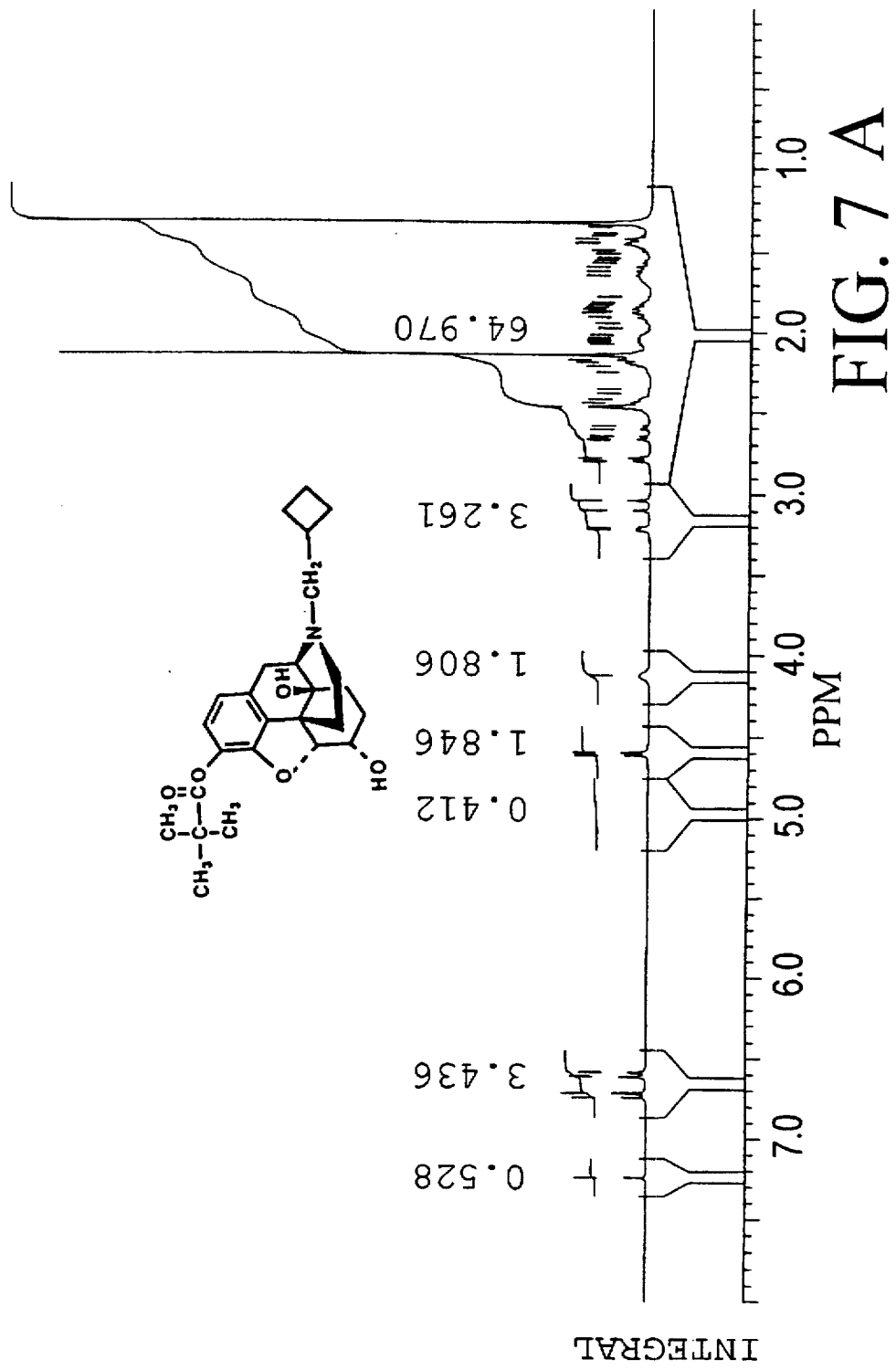
Figure 8A:
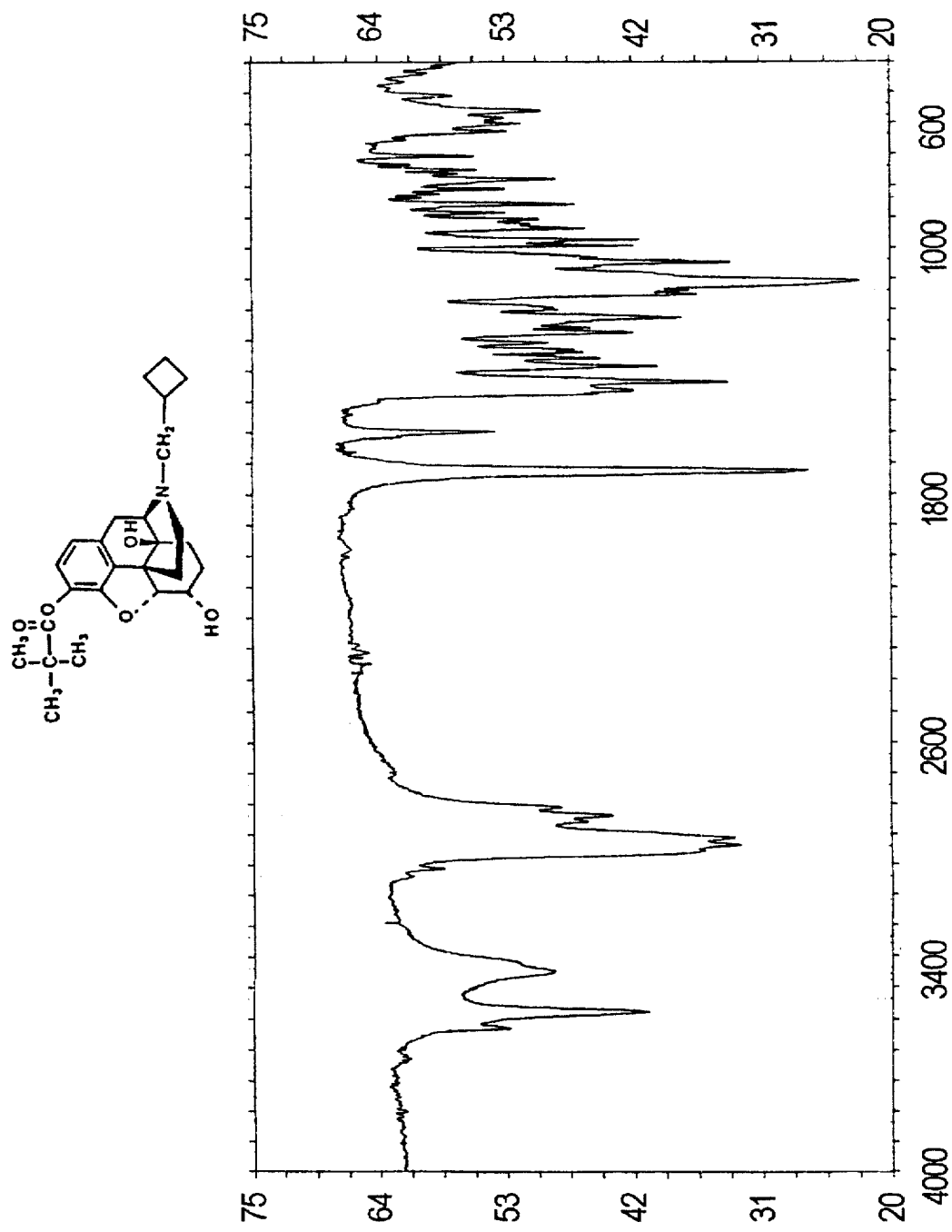

EXAMPLE 2
Preparation of Nalbuphine Pivalate 75 mL of methylene chloride and 3.75 g (0.01 mole) of nalbuphine were placed in a 250-mL ice-bathed round-bottomed flask. While stirring, 0.01 mole of pivaloyl chloride dissolved in 20 mL of methylene chloride was added gradually. Following the procedure as described in Example 1, pure nalbuphine pivalate was obtained. The physical data are shown in Table 1 and FIGS. 6, 7 and 8.

EXAMPLE 3
Preparation of Nalbuphine Benzoate

This compound was prepared according to the procedure of Example 1, by substituting 0.011 mole benzoyl chloride for anhydrous propionic anhydride. Pure nalbuphine benzoate was obtained. The physical data are shown in Table 1.

EXAMPLE 4
Preparation of Nalbuphine Enanthate

Figure 9A:
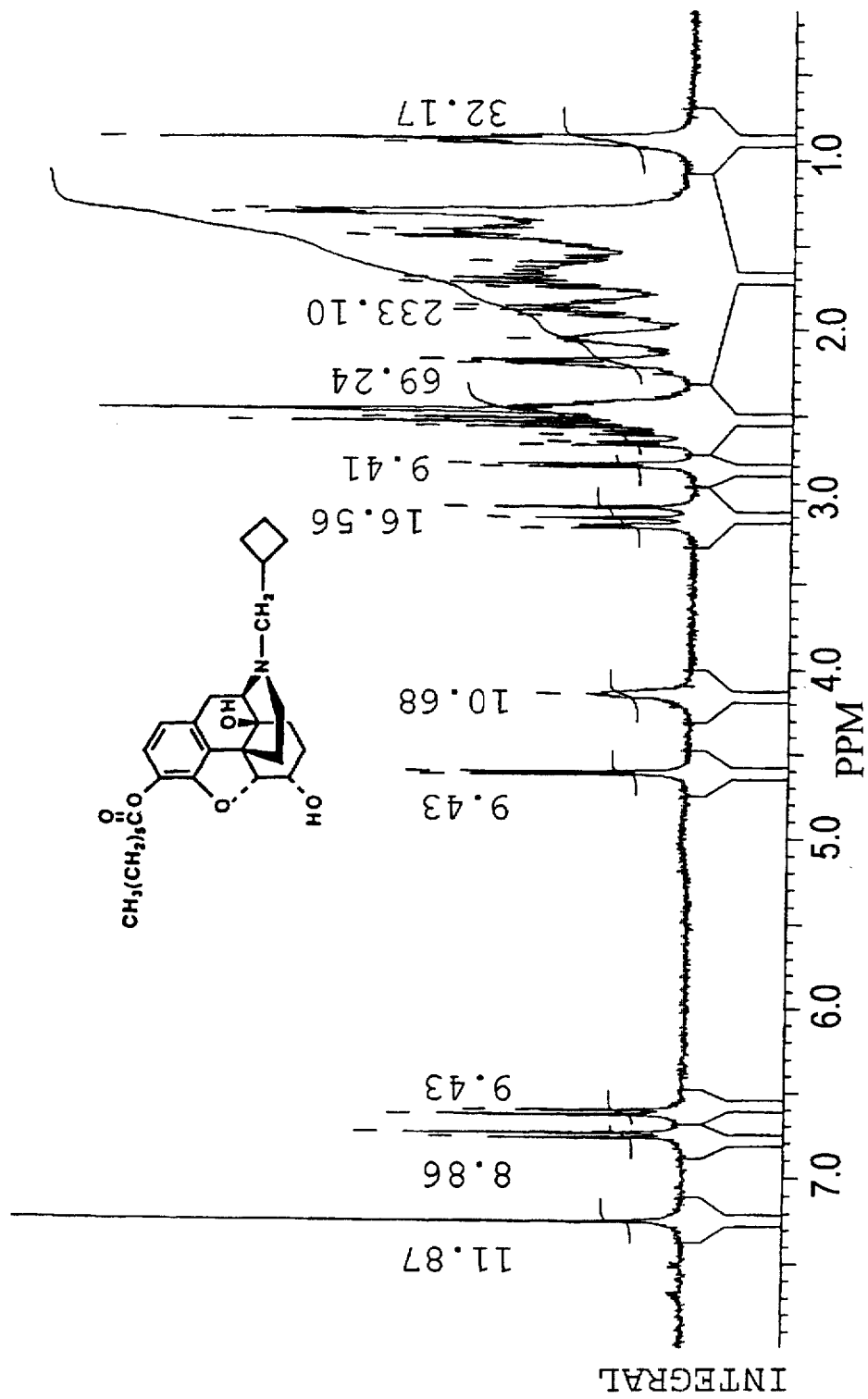

This compound was prepared according to the procedure of Example 1, by substitution of 0.011 mole heptanoyl chloride for anhydrous propionic anhydride. Pure nalbuphine enanthate was obtained. The physical data are shown in Table 1 and FIG. 9.

Figure 10A:
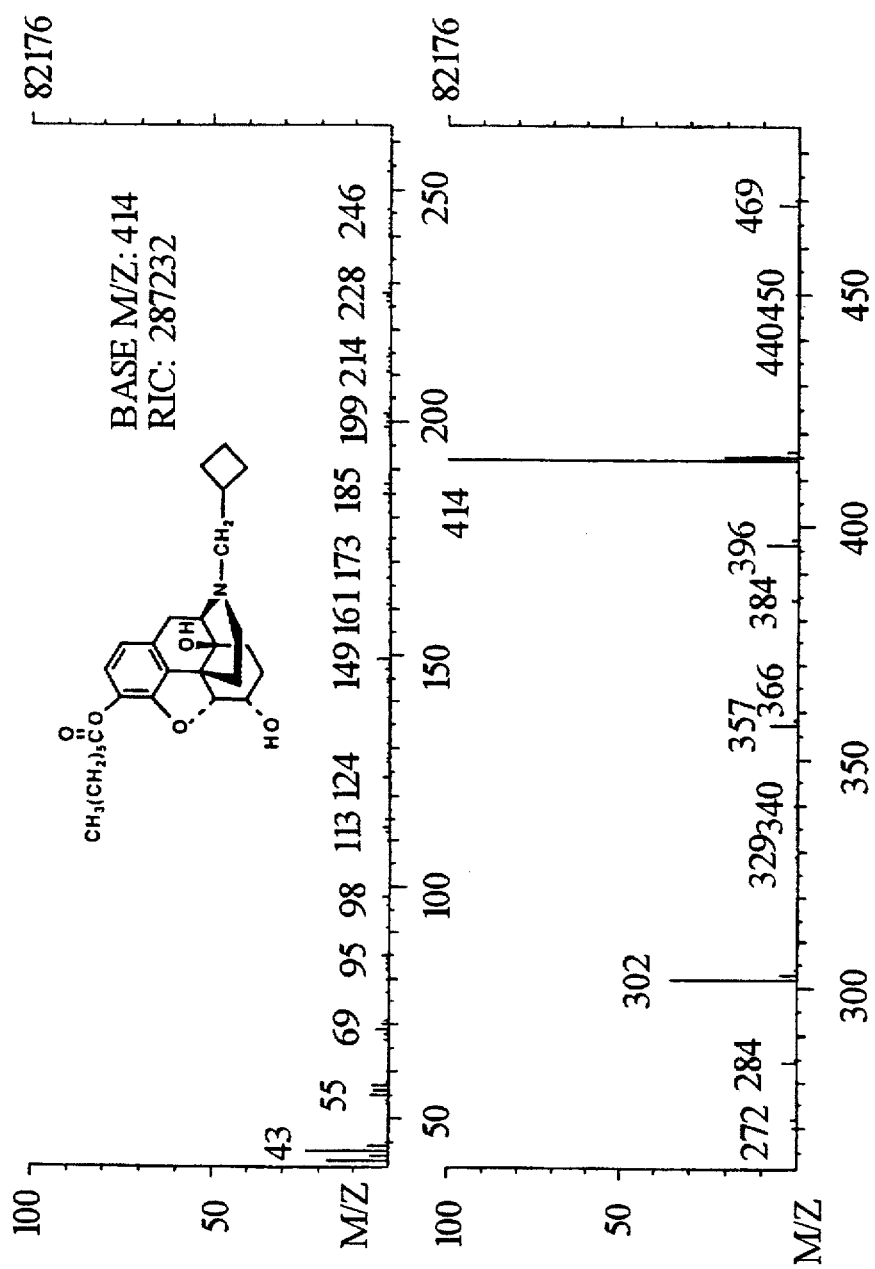

EXAMPLE 5
Preparation of Nalbuphine Decanoate This compound was prepared according to the procedure of Example 1, by substitution of the 0.011 mole decanoyl chloride for anhydrous propionic anhydride. Pure nalbuphine decanoate was obtained. The physical data are shown in Table 1 and FIG. 10.

EXAMPLE 6
Preparation of Nalbuphine Behenate

Figure 11A:
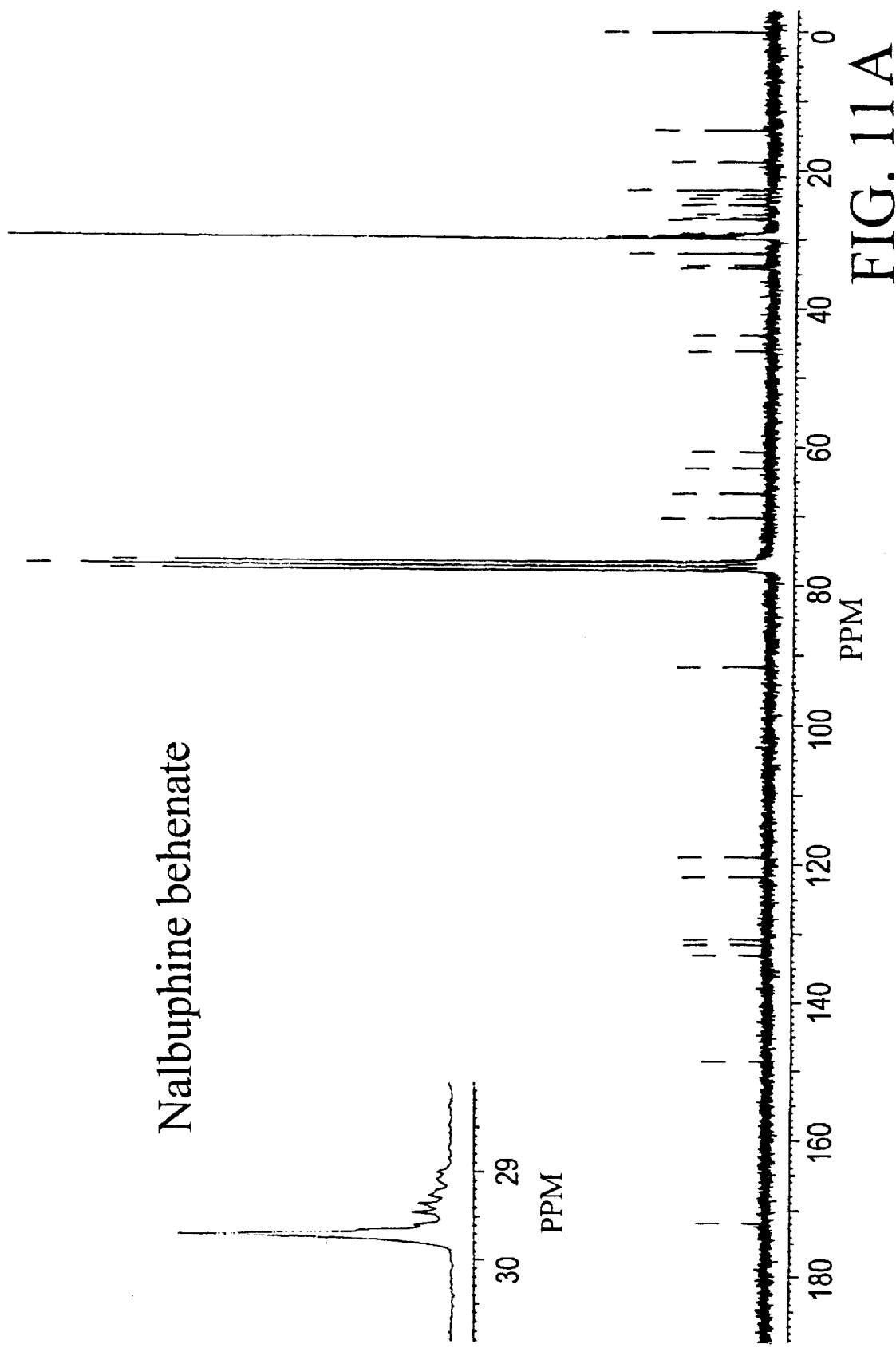

This compound was prepared according to the procedure of Example 1, by substitution of 0.35 g behenic anhydride for anhydrous propionic anhydride. Pure nalbuphine behenate was obtained. The physical data are shown in FIG. 11.

EXAMPLE 7
Preparation of Nalbuphine Erucicate

Figure 12A:
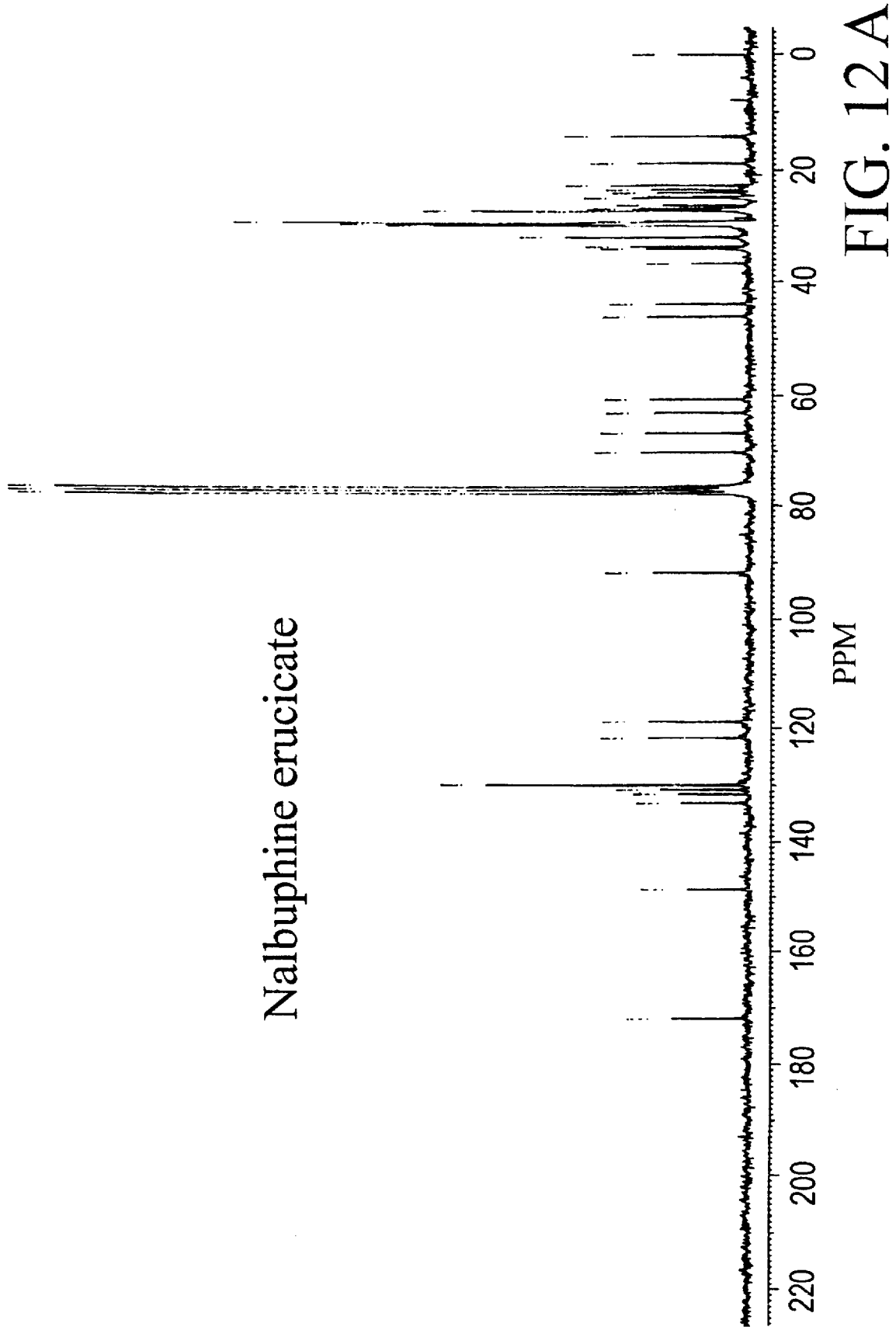

This compound was prepared according to the procedure of Example 1 by substituting 0.48 g erucic anhydride for anhydrous propionic anhydride. Pure nalbuphine erucicate was obtained. The physical data are shown in FIG. 12.

EXAMPLE 8
Preparation of Nalbuphine Arachidate

This compound was prepared according to the procedure of Example 1 by substitution of 0.85 g arachidic anhydride for anhydrous propionic anhydride. Pure nalbuphine arachidate was obtained. The physical data are shown in FIG. 13.

EXAMPLE 9
The Selection of Oil for Injection of Nalbuphine Prodrugs
Materials Sesame oil, soybean oil and an ethyl ester of peanut oil were tested in the present invention as the oil vehicles for the nalbuphine prodrugs. Phosphate buffer (monobasic potassium phosphate, 1.9 g, dibasic sodium phosphate, 8.1 g, sodium chloride 4.11 g were dissolved in 1 L water to make an isotonic solution of pH 7.4 and used as a control.

Experimental

Each experimental group has six samples. Into a dialysis bag were placed 50 mg (0.127 mmole) of nalbuphine hydrochloride or 45 mg (0.127 mmole) of nalbuphine free base and 1 mL of the oil vehicle or the phosphate buffer. The cut off of the dialysis bag was 12,000-14,000. A 250-mL of an iodine flask containing 150 mL of phosphate buffer was used to place the dialysis bag. Inside the flask, a magnetic stirrer bar was placed. The dialysis proceeded at a stirring speed of 500 rpm and the release rate of nalbuphine from each preparation was measured. A UV spectrometer (UV-160), Shimadzua, Kyoto, Japan) was used to detect the nalbuphine content in the phosphate buffer outside the bag.

Result

Figure 14:
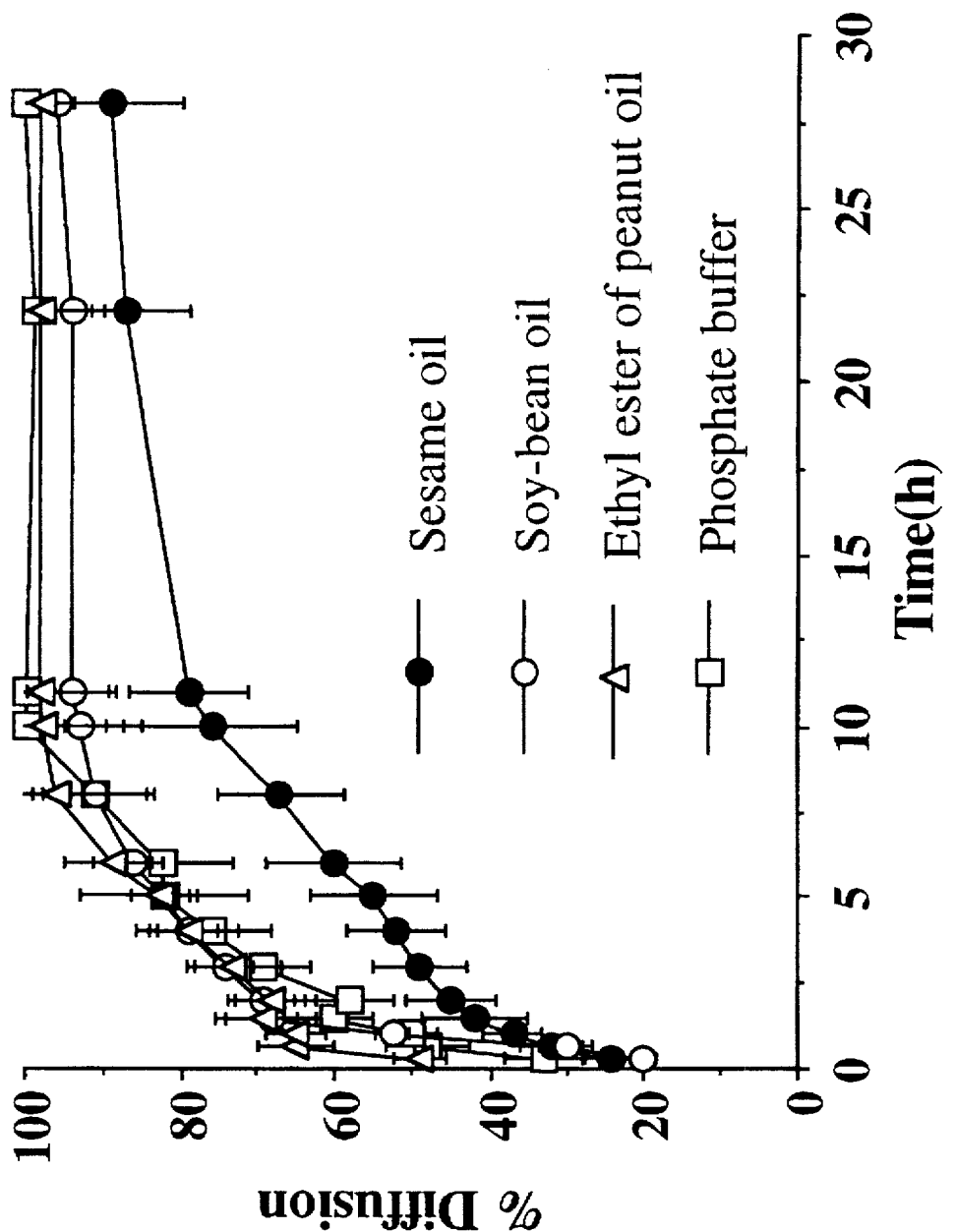
FIG. 14 illustrates the dialysis test of the release rate of nalbuphine HCl from oil-injection
Figure 15:
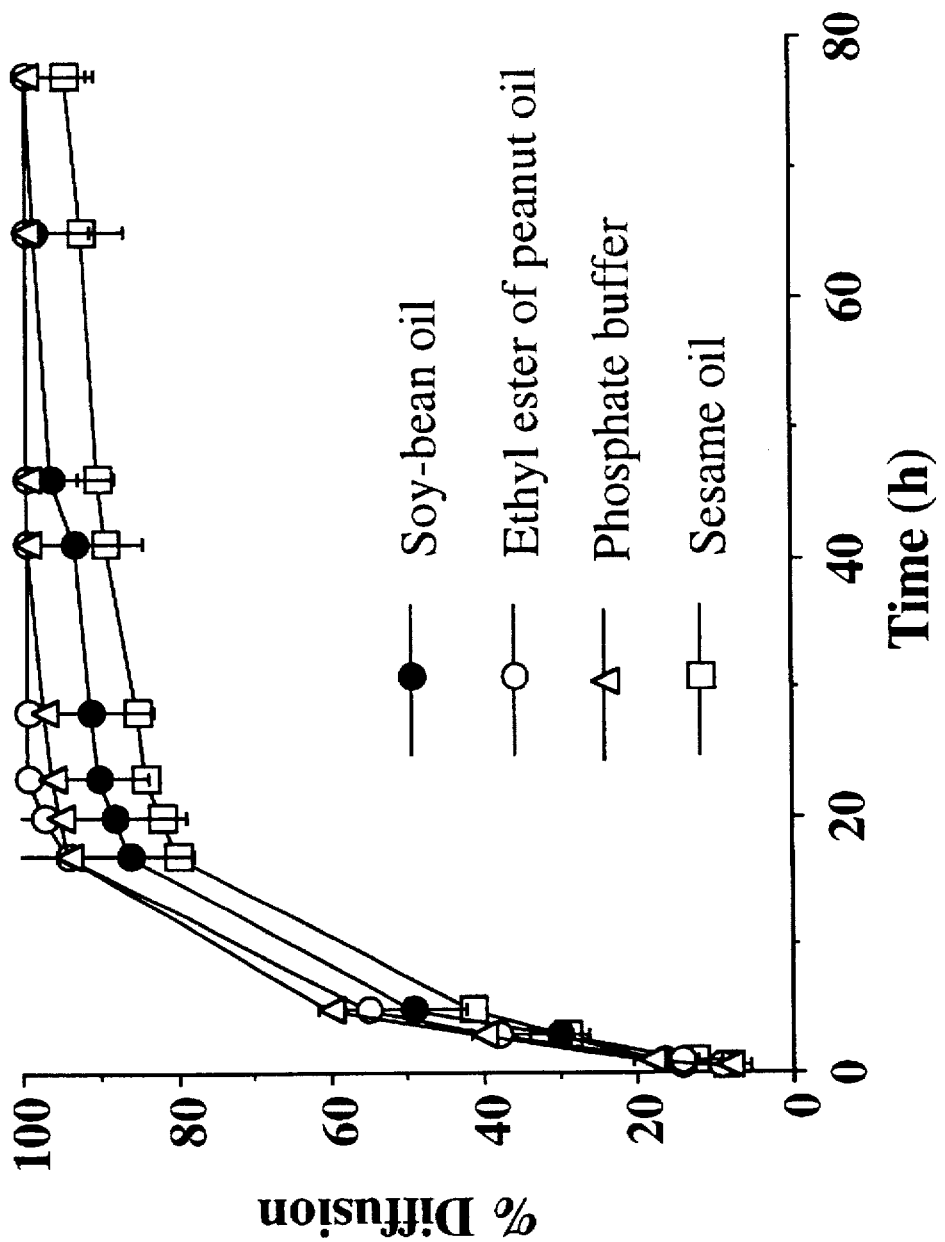
FIG. 15 illustrates the dialysis test of the release rate of nalbuphine free base from oil-injection
Figure 16:
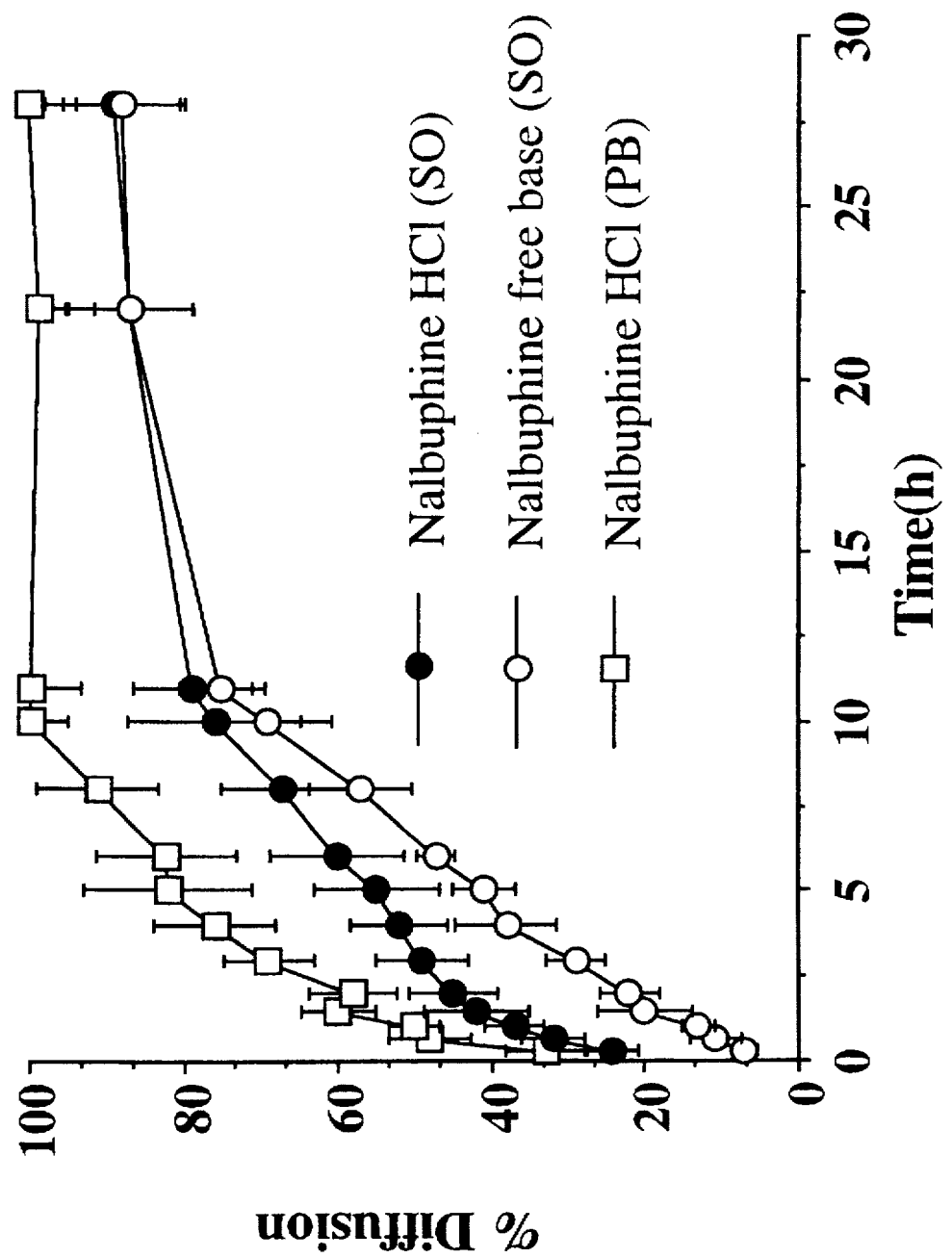
FIG. 16 illustrates dialysis test of the release rate of nalbuphine HCl or nalbuphine free base from sesame oil-injection FIG. 17 Dose-Response Curves of Nalbuphine Prodrugs FIG. 18 plasma concentration of Nalbuphine decanoate

The release profile of nalbuphine from each preparation and control group are shown in FIGS. 14, 15, and 16. As shown in FIG. 14, the preparation with sesame oil as the vehicle has the slowest release rate ($p<0.05$) and there is no significant difference within the other three preparations. FIG. 15 shows that the amount of released nalbuphine free base was less in the preparations with sesame oil than with peanut oil ester and the control between 17 and 28 hours ($p<0.05$). FIG. 16 shows the amount of nalbuphine released from preparation (a) nalbuphine hydrochloride dissolved in sesame oil, preparation (B) nalbuphine hydrochloride dissolved in phosphate buffer, and preparation (C) nalbuphine free base dissolved in sesame oil. After three hours the release in (B) is greater than (A) and (A) is greater than (C). After a period of between 3 and 28 hours (A) is greater than (C).

EXAMPLE 10
Preparation of Oily Injection Formulations Containing the Long-Acting Nalbuphine Prodrugs (1) 10.50 mgs of nalbuphine propionate was added to a 2.8 mL of sesame oil. The mixture was shaken slightly to effect complete dissolution.

(2) 11.91 mg of nalbuphine enanthate was added to a 2.8 mL of sesame oil. The mixture was shaken slightly to effect complete dissolution.

EXAMPLE 11
Preparation of Saturated Oily Injectable Suspensions of Long-Acting Nalbuphine Prodrugs 300 mg of nalbuphine enanthate was added to 2.8 mL of sesame oil (supersaturated). A saturated oil injectable suspension was obtained.

EXAMPLE 12
Preparation of Oral Capsules

To a mixture of 4.1 g of nalbuphine propionate and 10 mL of tetrahydrofuran, 2 mL of 20% hydrochloric acid alcoholic solution was added drop by drop. The monohydrochloride salt of nalbuphine propionate precipitated out. About 4.4 g of water soluble nalbuphine propionate monohydrochloride was thus obtained. The product was placed into hard gelatin capsules or other capsules for pharmaceutical use.

EXAMPLE 13
Preparation of Percutaneous Dosage Forms 470 mg of nalbuphine enanthate was added to an aqueous solution containing 50% of glycerin and 50% of 20 mg/mL methylcellulose to make a gel preparation by trituration.

EXAMPLE 14
In Vivo Pharmacodynamic Study Prodrugs (1) Animal Male, Sprague-Dawley rats (175–225 g) were used. Each group consisted of 6 rats and each rat was injected once intramuscularly on the rear leg.

(2) Material

A. The Dose-Response Curves (a) Nalbuphine hydrochloride doses of 100 mg/kg, 10 mg/kg, 0.5mg/kg, 0.1 mg/kg, 0.05 mg/kg, 0.01 mg/kg were used.

(b) Morphine hydrochloride, doses of 10 mg/kg, 5 mg/kg, 1 mg/kg, 0.5 mg/kg, 0.1 mg/kg, 0.05 mg/kg, 0.01 mg/kg were used.

(c) Buprenorphine hydrochloride, doses of 100 mg/kg, 10 mg/kg, 5 mg/kg, 1 mg/kg, 0.5 mg/kg, 0.1 mg/kg, 0.01 mg/kg were used.

B. The pharmacodynamic Study of Nalbuphine Prodrugs (a) 25 micromole/2.8 ml of nalbuphine hydrochloride in saline and nalbuphine base in sesame oil were used as controls. The dose for each rat was 25 micromole per kg, intramuscularly.

(b) 25 micromole/2.8 ml of Nalbuphine prodrugs in sesame oil were used for study. The dose for each rat was 25 micromole per kg, intramuscularly.

(3) Experimental

In this experiment, a circulating cold ethanol bath with a temperature maintained at $-20°$ C. was set up. After dosing, the rat tail (⅓ from the tip) was immersed in the bath. The latency for the rat to flick its tail from the bath was measured to be the nociceptive threshold. The effect of various opium alkaloid preparations can be determined with this test.

The nociceptive effect can be calculated as follows:

$$\text{The percentage of nociceptive effect} = \frac{\left[\begin{array}{c}\text{The latency}\\\text{after dosing}\end{array}\right] - \left[\begin{array}{c}\text{The latency}\\\text{before dosing}\end{array}\right]}{\left[\begin{array}{c}\text{experimental}\\\text{end}\end{array}\right] - \left[\begin{array}{c}\text{The latency}\\\text{before dosing}\end{array}\right]} \times 100$$

35, 25, 15 minutes before dosing, Male Sprague Dawley rats were tested to measure the basic response latency. The time to stop the experiment was set at 40 sec. to prevent the tail from cold sore. No cold sores were found in 40 sec. Five minutes after the drug was given to the rat, the flick test was performed every 10 minutes or more.

(4) Results

A. The Dose-Response Curves

The maximal analgesic effect for intramuscular injection was found at 0.05 to 10 mg/kg for morphine hydrochloride, 0.1 to 100 mg/kg for nalbuphine hydrochloride, 0.1 to 100 mg/kg for buprenorphine hydrochloride.

B. The Pharmacodynamic Study of Nalbuphine Prodrugs

Figure 17:
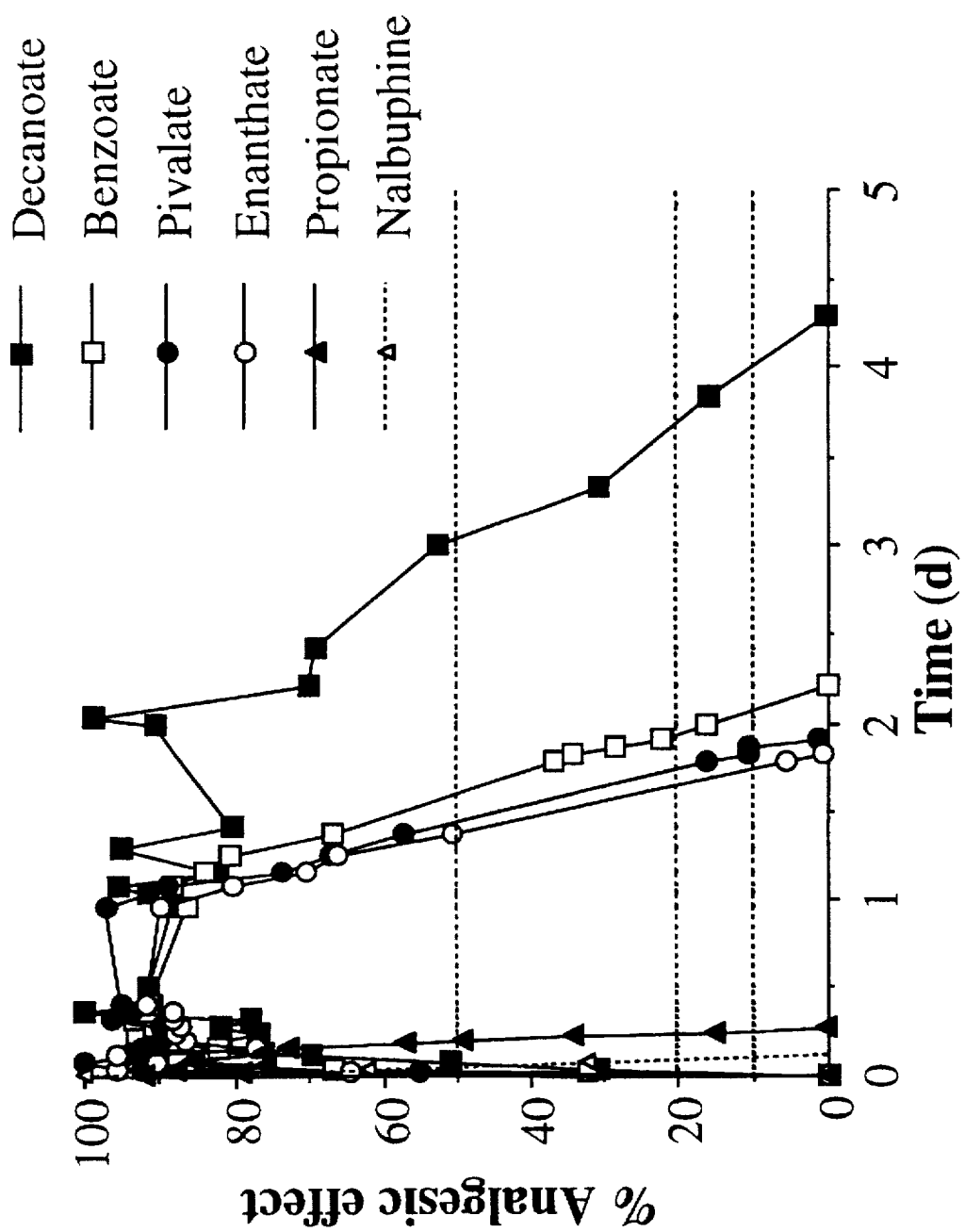

The lipophilicity of nalbuphine base is enhanced when it is prepared from nalbuphine hydrochloride, in FIG. 16 the release times are significantly increased. The 50% analgesic effect for human intramuscular injection found at 0.8 nmole/kg is 2.5 hours (the rats at 25 nmole/kg is 1.1 hours). The 20% analgesic effect for humans is 4.4 hours (the rat is 2.1 hours). The 10% analgesic effect for humans is 5.0 hours (the rat is 2.4 hours). As shown in FIG. 17, the 50% analgesic effect of nalbuphine hydrochloride is 2.5 hours, the nalbuphine propionate is 10 hours, the longest duration is 6.7 days of nalbuphine decanoate. As the 10% analgesic effect of nalbuphine hydrochloride is 12 hours, the longest duration is 8.2 days of nalbuphine decanoate.

TABLE 1

| | R | | MW | MF | MP |
|---|---|---|---|---|---|
| Nalbuphine | H | | 357.46 | $C_{21}H_{27}NO_4$ | 226° C. |
| N-Decanoate | $CH_3(CH_2)_8C-$ | 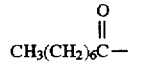 | 511.70 | $C_{31}H_{45}NO_5$ | 83° C. |
| N-Enanthate | $CH_3(CH_2)_5C-$ | 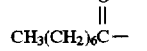 | 469.61 | $C_{28}H_{39}NO_5$ | 78° C. |
| N-Benzoate | | 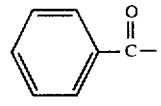 | 461.55 | $C_{28}H_{31}NO_5$ | 171° C. |
| N-Propionate | $CH_3CH_2C-$ | 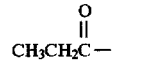 | 413.51 | $C_{24}H_{31}NO_5$ | 144° C. |
| N-Pivalate | | 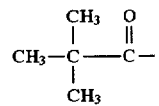 | 441.59 | $C_{26}H_{36}NO_5$ | 94° C. |

TABLE 2

| | % Analgesic effect | | |
|---|---|---|---|
| | 50% | 20% | 10% |
| Nalbuphine HCl | 2.5 Hour | 4.4 H | 5.0 H |
| N-Decanoate | 6.7 Days | 7.5 D | 8.2 D |
| N-Benzoate | 3.5 Days | 4.0 D | 4.0 D |
| N-Pivalate | 3.2 Days | 3.6 D | 3.8 D |
| N-Enanthate | 3.9 Days | 3.4 D | 3.6 D |
| N-Propionate | 10 Hours | 11 H | 12 H |

EXAMPLE 15
Paw Pressure test (1) Animal Male, New Zealand white rabbits (2.4–2.6 Kg) were used. Each group consisted of 3 rabbits and each rabbit was injected once intramuscularly on the long ears.

(2) Material (a) Nalbuphine hydrochloride doses of 20 mg/kg, 10 mg/kg, 5 mg/kg, 2 mg/kg were used.

(b) nalbuphine decanoate doses of 0.25 mg/kg were also used.

(3) Experimental

In this experiment, 35, 25, 15 minutes before dosing, the male rabbits' paws were tested to measure the basic response latency. The time to stop the experiment was set at 50% pressure over of the basic response latency before dosing to prevent impairment of health and 5–10 minutes after dosing, 1 ml blood was collected and assayed by a HPLC method.

(4) Results

The maximal analgesic effect can be calculated as follows:

$$\text{The percentage of analgesic effect} = \frac{\begin{bmatrix}\text{The latency of}\\\text{experimental}\end{bmatrix} - \begin{bmatrix}\text{The latency of}\\\text{basic response}\end{bmatrix}}{\begin{bmatrix}\text{The latency}\\\text{of end}\end{bmatrix} - \begin{bmatrix}\text{The latency of}\\\text{basic response}\end{bmatrix}} \times 100$$

Figure 18:
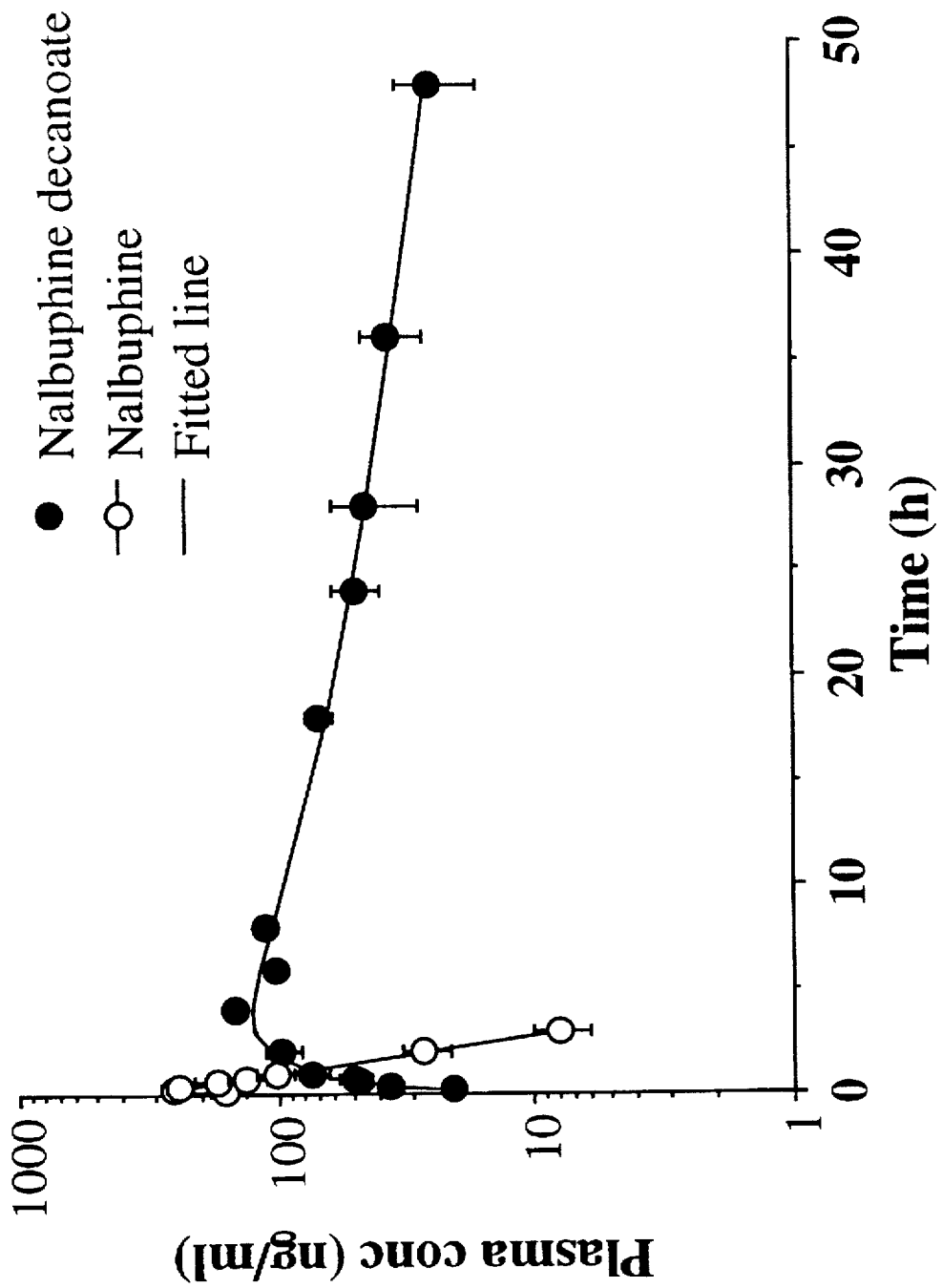

The half time of plasma concentration was found to be 1560 minutes for nalbuphine decanoate, and 51 minutes for nalbuphine hydrochloride. The duration of nalbuphine decanoate was increased 30 times over the nalbuphine hydrochloride as shown in FIG. 18.

Figure 19:
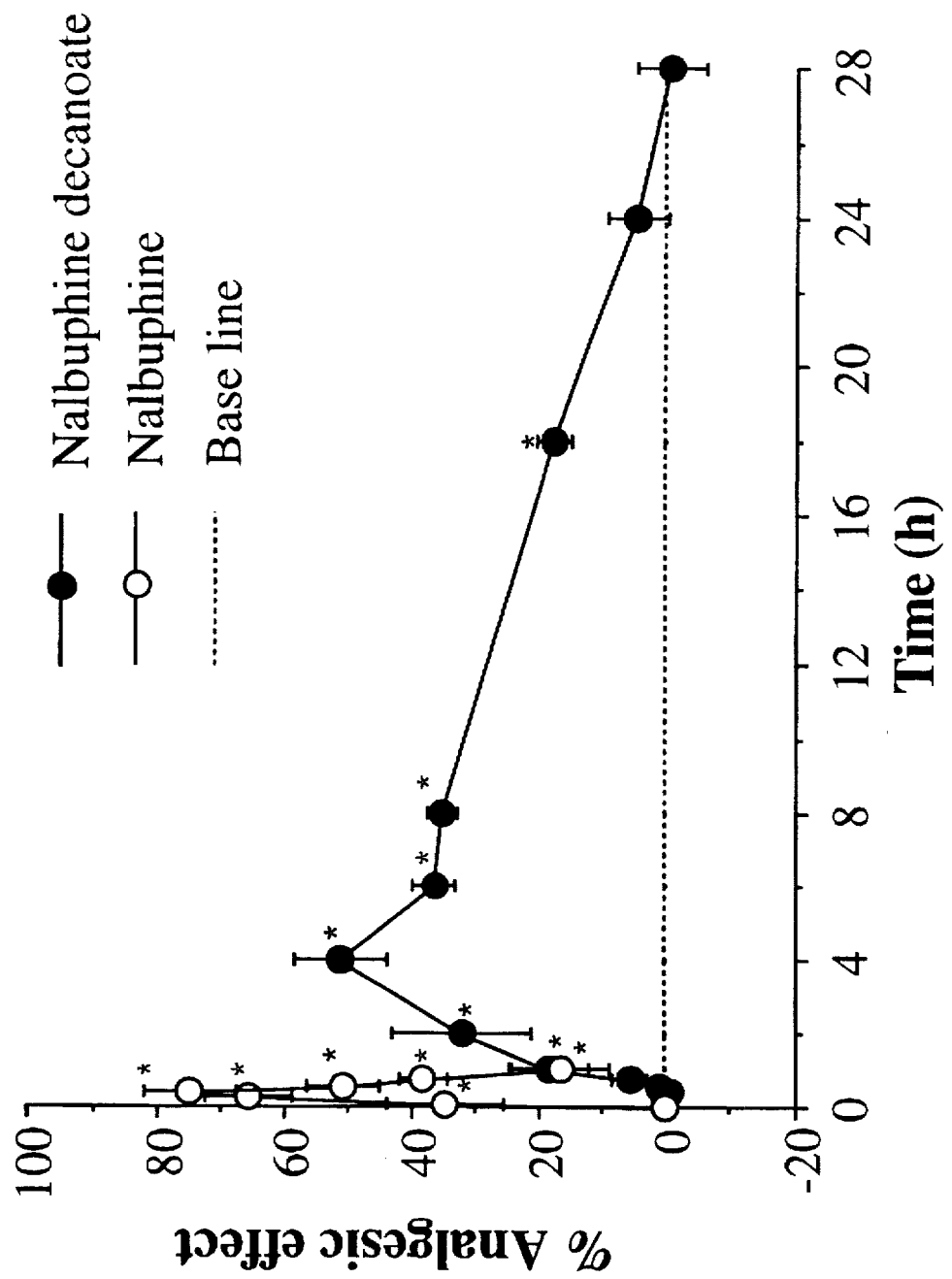
FIG. 19 illustrates the analgesic effect for intramuscular injection of Nalbuphine decanoate

The analgesic effect for intramuscular injection was found at 45 minutes for 10 mg/kg (25 mmole/kg) of nalbuphine hydrochloride, and 18 hours for 0.25 mmole/kg of nalbuphine decanoate as shown in FIG. 19.

EXAMPLE 16
Percutaneous Transport Study (1) Animal Male, New Zealand white rabbits (1 Kg) were used.

(2) Material (a) 5% nalbuphine decanoate in jel of 2% CMC Na (b) 5% nalbuphine decanoate in jel of 2% CMC Na, 10% terpineol (3) Experimental In this experiment, the transdermal penetration of material was measured across full-thickness female rabbit skin in vitro. Abdominal skin from New Zealand white rabbits was excised in two pieces at sacrifice and used immediately. The adherent fat and other visceral debris were removed from the undersurface. The skin with an available diffusion area of 0.72 cm$^2$ separated the donor and receptor chambers of modified Franz diffusion cells. The sampling arm was moved to close the skin to avoid possible air bubble accumulation. Also the bottom of the cell was flattened to smooth the stirring process. The diffusion cells were thermostated at 37° C. throughout the experiment. The receptor compartment of each cell was filled with 5.5 ml of normal saline containing streptomycin sulfide (50 mg/liter) and penicillin G potassium salt (30 mg/liter) and stirred with a magnetic stirrer (600 rpm). At the start of the experiment a 0.5 g material gel was applied to the exposed epidermal skin surface in the donor phase of the diffusion cell. Subsequently, hourly samples ($^{200}$ μl ) up to 72 hrs. of the receptor perfusate were collected and assayed by a HPLC method. The withdrawn volume was replaced with fresh medium.

(3) Results

Figure 20:
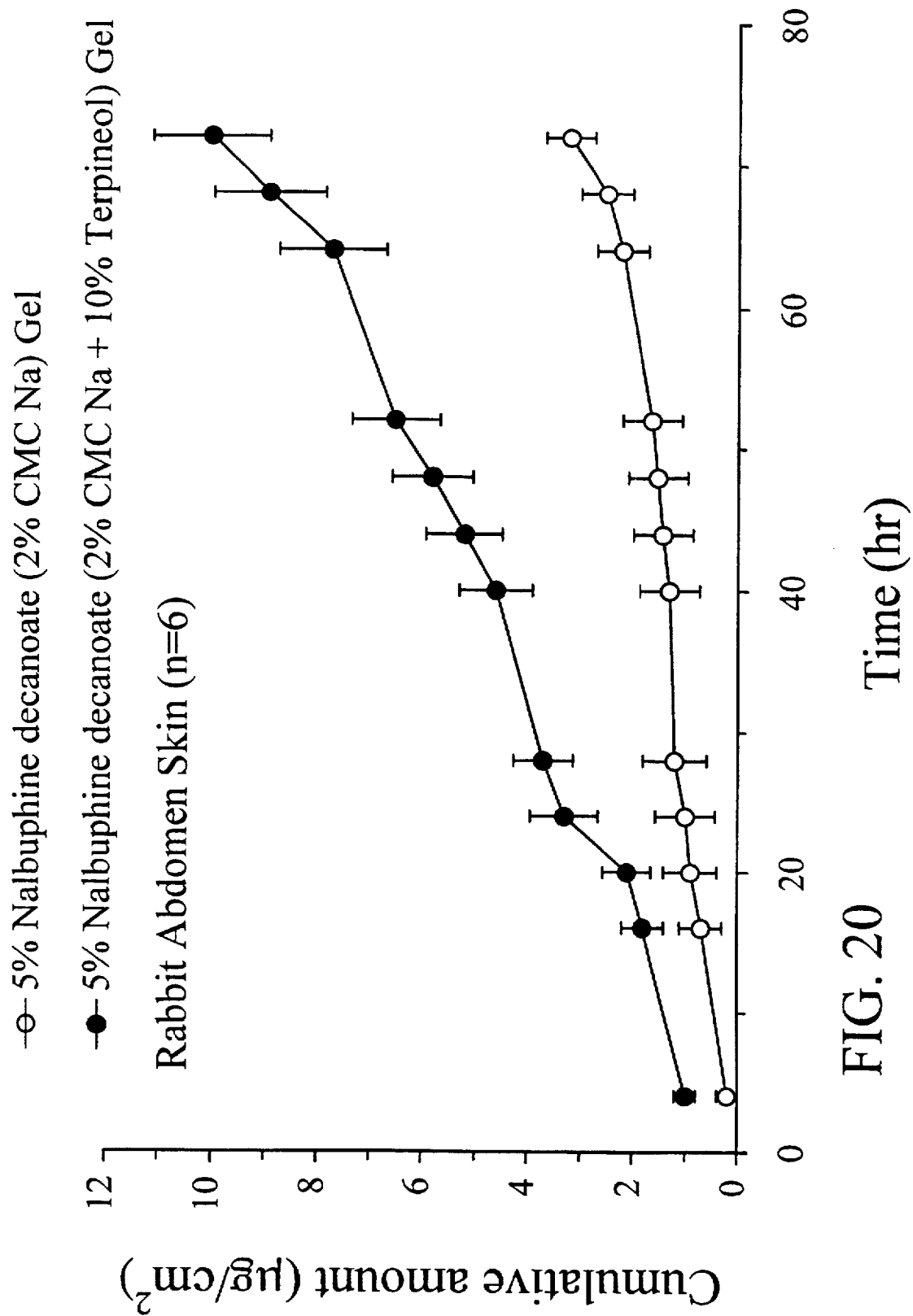
FIG. 20 shows the transdermal penetration of Nalbuphine decanoate

Shown in FIG. 20, the typical cumulative amount under 24 hours is 1.04±0.30 μg/cm$^2$, under 48 hours is 1.67±0.38 μg/cm$^2$, under 72 hours is 3.17±0.35 μg/cm$^2$. The cumulative amount of the jel which containing 10% terpineol under 24 hours is 3.31±0.45 μg/cm$^2$, under 48 hours is 5.78±0.81 μg/cm$^2$, under 72 hours is 9.87±1.44 μg/cm$^2$.

Pharmacodynamic Study of Nalbuphine Arachidate

Nalbuphine, a kappa-receptor agonist and mu-receptor antagonist opiod analgesic, not only possesses a potent analgesic effect but also minimizes the side effects, such as tolerance, dependence, respiratory depression that traditional opiods have. It has been extensively used by oral, intramuscular, intravenous, or by other administration routes for the treatment of various pain symptoms. However, like other opiods, nalbuphine has a short duration of action so that it is not suitable for the treatment of clinical pain with long duration. Our research group have synthesized a nalbuphine prodrug, nalbuphine arachidate which is dissolved in the injectable sesame oil as an oily suspension dosage form to determine whether it would provide a long duration of analgesic effect. The object of the present study was to evaluate the analgesic effect and the duration of action of nalbuphine arachidate in rats.

Male Sprague-Dawley rats (175–225 g) provided by the National Defense Medical Center, Taiwan, were housed in cages (n=3 for each 47×21×26 cm$^3$ cage) at controlled room temperature 22°±1° C., humidity 50±10% and artificial light 06:00–8:00 h. The rats had continuous access to food and water. They were carried out only after they had acclimated to the above environment for at least 7 days. All tests were performed in accordance with the recommendations and policies of the International Association for the Study of Pain and were approved by our institutional animal investigative committee.

Drugs

The following drugs and dosages were used: Nalbuphine HCl (Du Pont, Merck, U.S.A.) 25 μM/kg, and nalbuphine arachidate 25 μM/kg. Nalbuphine HCl was dissolved in 0.9% saline. Nalbuphine arachidate was prepared in sesame oil as an oily suspension dosage form. All drugs were injected intramuscularly into the left hind leg.

Experimental Procedure

Fourteen male Sprague-Dawley rats were randomly divided into two groups (n=7, each) and received one of the following treatments: 1. nalbuphine HCl 25 μM/kg, 2. nalbuphine arachidate 25 μM/kg. Each rat received only one injection. Gentle manipulation was done during the study and the test took place in a separate, sound attentuated room in which no other rats were present in order to minimize the variability of the study.

The antinociceptive activity was assessed using the cold ethanol tail-flick test. The testing temperature was set at 20° C. and the cutoff time was 40 seconds. All rats were tested at 35, 25, and 15 min before medication. To minimize the variability, the first datum was discarded and the remaining two were averaged to obtain a baseline reading. Measurements of the antinociceptive thresholds of nalbuphine and nalbuphine arachidate were done 20 minutes or even longer after intramuscular administration of different formula.

Statistical Analysis

Results are expressed as mean ±S.E.M. Analysis of variance and Dunnett test were used when comparing the antinociceptive effect with baseline value before treatment. A P value less than 0.05 was considered significant.

Results

Figure 22:
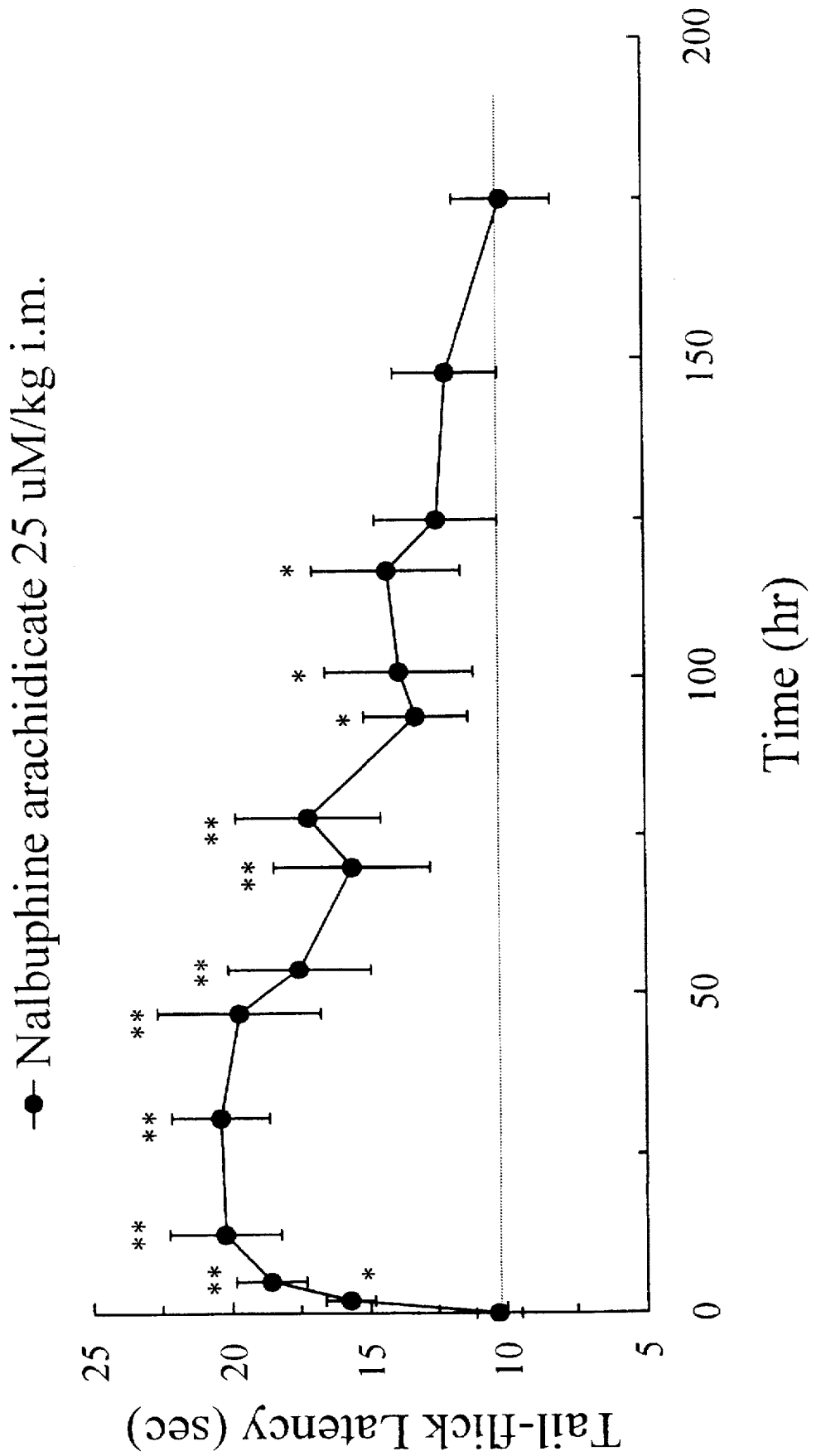
FIG. 22 is a response-time curve of nalbuphine arachidate by the cold ethanol tail flick test
Figure 23:
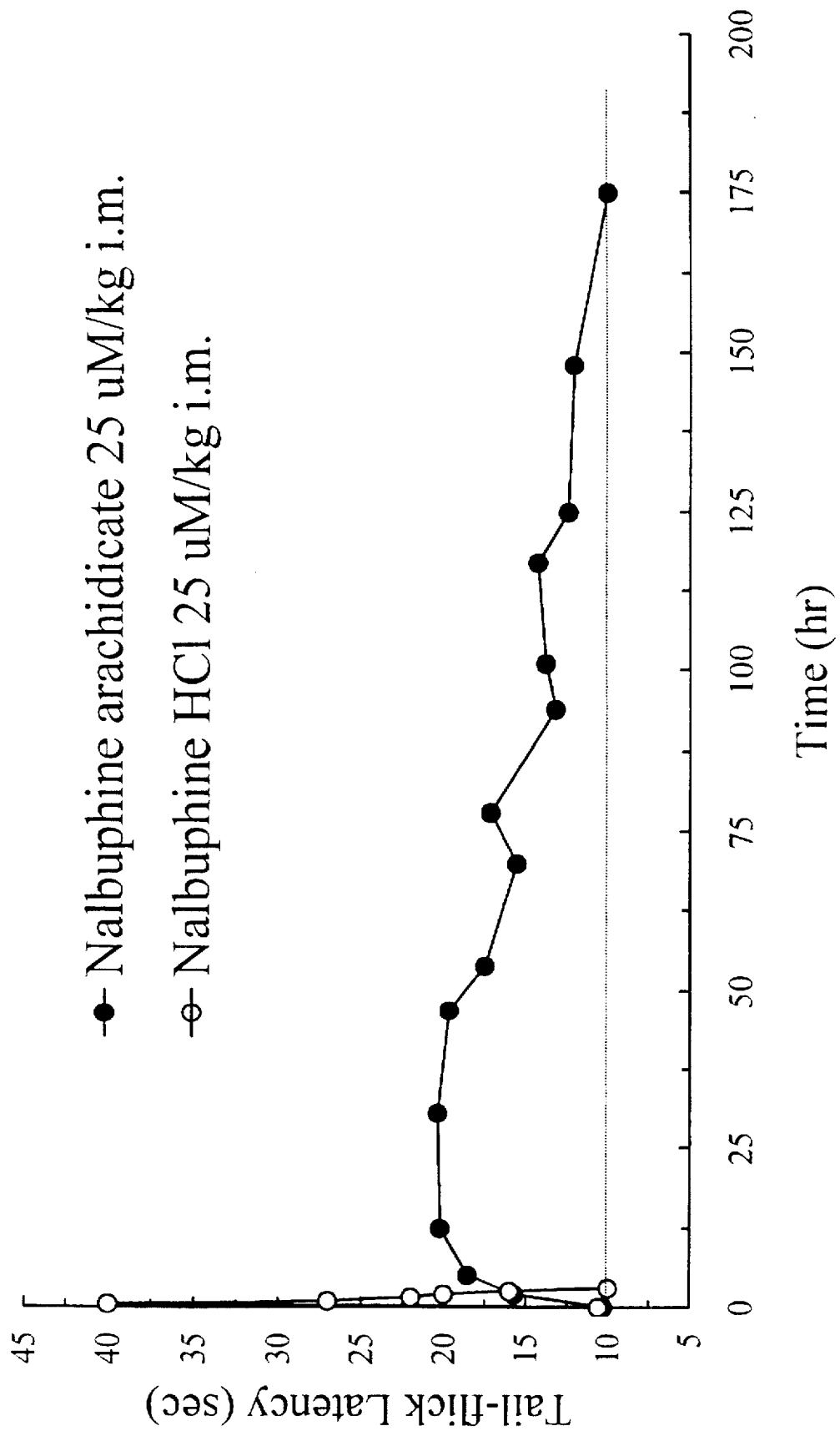
FIG. 23 is a comparison of the analgesic duration of nalbuphine HCl and nalbuphine arachidate This present invention also covers the process of preparation of the ester-type nalbuphine prodrugs shown in FIG. (1). Nalbuphine esters are synthesized by the following steps: (1) chlorinate the hydroxyl group of nalbuphine base by reacting with methylene chloride, (2) react with triethylamine which is dissolved in methylene chloride, (3) carry out the esterification by reacting with fatty acid anhydrides or acid chlorides, and (4) purify the above product by silica chromatography. In the alternative, the nalbuphine esters may also be obtained by the general method of preparing esters from alcohols or phenols, for instance, by reacting the hydroxyl group of nalbuphine with acid chlorides, acid anhydrides, carboxylic acids, esters, or sulfonyl chlorides.

This study has shown that both nalbuphine HCl and nalbuphine arachidate provide significant analgesic effects (see FIGS. 21 and 22), but the analgesic effect of nalbuphine arachidate is longer than that of nalbuphine HCl as shown in FIG. 23. The analgesic effect of nalbuphine HCl (25 μM/kg) is 4 hours, but, the analgesic effect of nalbuphine arachidate is around 4–5 days.

Figure 21:
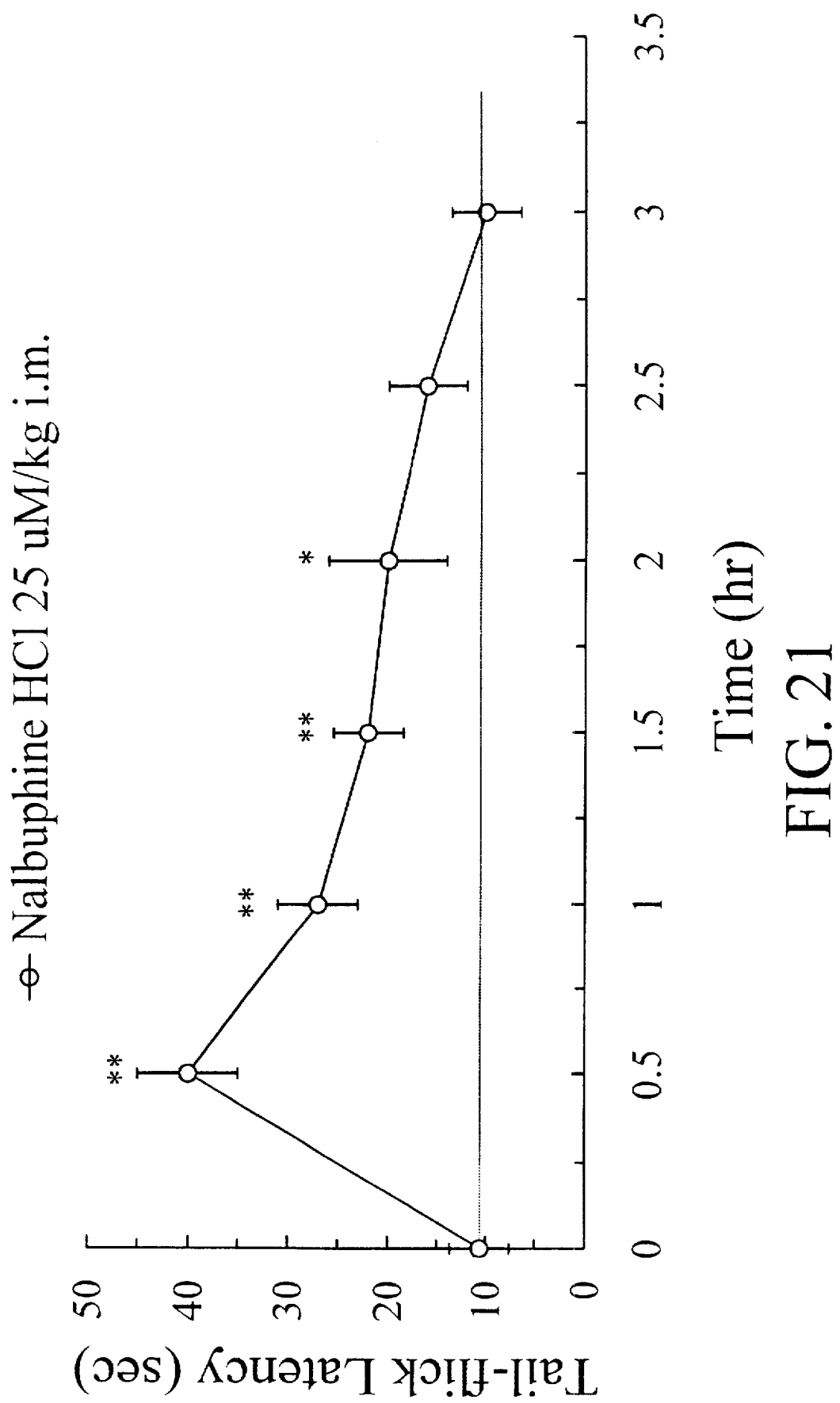
FIG. 21 is a response-time curve of Nalbuphine HCl

In FIG. 21 Response-time curves of nalbuphine HCl by the cold-ethanol tail-flick test. After an intramuscular injection of different doses of nalbuphine HCl in rats (n=7), measurements of analgesic effect were made. Each rat received only one injection. The testing temperature was set to be −20° C. and the cutoff time was 40 sec. Data are shown as mean ±1 S.E.M., *p<0.05, **p<0.01 when compared to pretest value using ANOVA followed by Dunnett test.

S.E.M. means: Standard error or standard deviation of mean ANOVA is analysis of variance (frequently abbreviated to ANOVA and is an extremely powerful statistical technique which can be used to separate and estimate the different causes of variation p means probability Dunnett test is a posteriori comparison among means following an ANOVA. This test allows one to make all possible comparisons among groups.

FIG. 22 Response-time curves of nalbuphine arachidate by the cold ethanol tail-flick test. After an intramuscular injection of nalbuphine arachidate 25 μM/kg of nalbuphine arachidate in rats (n=7), measurements of the analgesic effects were made. Each rat received only one injection. The testing temperature was set to be −20° C. and the cutoff time was 40 sec. Data are shown as mean ±1 S.E.M., *p<0.05, **p<0.01 when compared to pretest value using ANOVA followed by Dunnett test. The meanings of S.E.M, p, ANOVA and the Dunnett test are as in FIG. 21.

FIG. 23 shows the analgesic duration of intramuscular nalbuphine HCl solution 25 μM/kg and nalbuphine arachidate oily suspension 25 μM/kg in rats.

Discussion

This study has shown that nalbuphine arachidate has a long duration of analgesic effect. The analgesic duration of a 25 μM/kg intramuscular injection was 4–5 days. This is a very important and valuable finding for pain management. In clinical study, the analgesic duration of an intramuscular injection of nalbuphine HCl 10 mg/65 kg (0.154 mg/kg) is 2–3 hours in a 65-kg patient. In our study, the analgesic duration of an intramuscular injection of 25 μM/kg (9.86 mg/kg) nalbuphine HCl is about 2 hours in rats. After comparing the analgesic duration and the doses used in humans and rats, we found that humans consume less nalbuphine than rats to obtain an equal analgesic duration. The ratio is about 1/16 folds (=9.86 mg/kg/0.154 mg/kg). According to the ratio, it is estimated that nalbuphine arachidate 1.56 μM/kg (=25 μM/kg/16) can provide a 4–5 days duration of analgesic effect in humans. The duration of pain relief is quite similar to the duration of clinical acute pain, such as postoperative pain, traumatic pain and burn pain. Since one injection of nalbuphine arachidate can provide a 4–5 day duration of analgesic effect, it may be very convenient for pain management, especially in the treatment of acute pain. Further, multiple-dose injections of nalbuphine arachidate may relieve most of the chronic pain, such as nonmalignant pain and cancer pain.

In conclusion, this study has shown that nalbuphine arachidate has a very long duration of analgesic effect after an intramuscular injection. The analgesic duration is 4–5 days in rats with a dose of 25 μM/kg. In addition, the analgesic duration is calculated to be 4–5 days in humans with a dose of 1.56 μM/kg intramuscularly.

What is claimed is:

1. A method of treating severe, acute, long lasting pain with a duration of relief of at least 10 hours up to 30 times the duration of action of nalbuphine hydrochloride in a living subject in need thereof, consisting of orally, intramuscularly, transdermally, or subcutaneously administering to said living subject a pharmaceutical composition which comprises an effective amount of an ester of nalbuphine of the formula

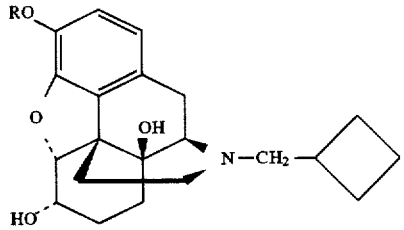

as the free base, or a salt thereof, wherein R is $R^1CO-$ and $R^1$ is a straight or branched alkyl group of 2–36 carbon atoms or a phenyl group, together with a pharmaceutically acceptable oil carrier.

2. The method according to claim 1 wherein said $R^1$ group is saturated or unsaturated alkyl.

3. The method according to claim 1 wherein R' is an alkyl group of 2–22 carbon atoms.

4. The method according to claim 1 wherein said composition is in suspension or solution in said oil.

5. The method according to claim 4 wherein said oil is sesame oil, soybean oil or the ethyl ester of peanut oil.

6. The method according to claim 1 wherein said composition is injected into the spinal marrow or into the cerebrospinal fluid.

7. The method according to claim 1 wherein said ester of nalbuphine is nalbuphine propionate.

8. The method according to claim 1 wherein said ester of nalbuphine is nalbuphine pivalate.

9. The method according to claim 1 wherein said ester of nalbuphine is nalbuphine enanthate.

10. The method according to claim 1 wherein said ester of nalbuphine is nalbuphine decanoate.

11. The method according to claim 1 wherein said ester of nalbuphine is nalbuphine behenate.

12. The method according to claim 1 wherein said ester of nalbuphine is nalbuphine erucicate.

13. The method according to claim 1 wherein said ester of nalbuphine is nalbuphine arachidate.

14. The method according to claim 1 wherein said ester of nalbuphine is nalbuphine benzoate.

15. The method according to claim 1 wherein said severe, acute long lasting pain is caused by cardiac, pulmonary, osteopathia, obstetrical surgery, burn injury or terminal stage of cancer.

* * * * *